United States Patent
Jung et al.

(10) Patent No.: US 12,247,242 B2
(45) Date of Patent: Mar. 11, 2025

(54) METHOD FOR QUANTITATIVELY CONTROLLING PLASMID COPY NUMBER IN ANTIBIOTIC-FREE PLASMID MAINTENANCE SYSTEM

(71) Applicants: POSTECH ACADEMY-INDUSTRY FOUNDATION, Gyeongsangbuk-do (KR); SEOUL NATIONAL UNIVERSITY R & DB FOUNDATION, Seoul (KR)

(72) Inventors: Gyoo Yeol Jung, Gyeongsangbuk-do (KR); Sang Woo Seo, Seoul (KR); Chae Won Kang, Daegu (KR); Hyun Gyu Lim, Chungcheongbuk-do (KR)

(73) Assignees: SEOUL NATIONAL UNIVERSITY R&DB FOUNDATION, Seoul (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 186 days.

(21) Appl. No.: 16/500,637

(22) PCT Filed: Apr. 5, 2018

(86) PCT No.: PCT/KR2018/004038
§ 371 (c)(1),
(2) Date: Oct. 19, 2023

(87) PCT Pub. No.: WO2018/186704
PCT Pub. Date: Oct. 11, 2018

(65) Prior Publication Data
US 2024/0200108 A1    Jun. 20, 2024

(30) Foreign Application Priority Data
Apr. 6, 2017  (KR) ................. 10-2017-0044979

(51) Int. Cl.
*C12N 15/70* (2006.01)
*C12P 5/02* (2006.01)
*C12P 7/46* (2006.01)

(52) U.S. Cl.
CPC ............. *C12P 7/46* (2013.01); *C12N 15/70* (2013.01); *C12P 5/026* (2013.01); *C12N 2800/101* (2013.01); *C12N 2830/36* (2013.01); *C12N 2840/10* (2013.01)

(58) Field of Classification Search
None
See application file for complete search history.

(56) References Cited

U.S. PATENT DOCUMENTS

| | | | |
|---|---|---|---|
| 2002/0061569 A1* | 5/2002 | Haselbeck | A61K 31/7088 435/325 |
| 2003/0204075 A9* | 10/2003 | Wang | C12Q 1/6883 536/24.3 |
| 2007/0150978 A1* | 6/2007 | Byrum | C07K 14/415 536/23.6 |
| 2016/0060660 A1* | 3/2016 | Hiller | C12N 9/88 435/252.32 |
| 2017/0202979 A1* | 7/2017 | Chakraborty | C12N 15/67 |
| 2019/0062760 A1* | 2/2019 | Du | C12N 15/635 |

FOREIGN PATENT DOCUMENTS

WO    WO-2010075441 A1 * 7/2010 ............. C12N 15/63

OTHER PUBLICATIONS

Martínez-García E, Benedetti I, Hueso A, de Lorenzo V. 2015. Mining environmental plasmids for synthetic biology parts and devices. Microbiol Spectrum 3(1):PLAS-0033-2014. doi:10.1128/microbiolspec.PLAS-0033-2015. (Year: 2015).*
Genbank KM234321.1 (NCBI GenBank: KM234321.1: Boolean integrase logic vector NAND gate BCD-RFP, complete sequence (Jun. 8, 2015) (Year: 2015).*
GenBank: CP007601.1 2015. Accession No. CP007601, *Staphylococcus capitis* subsp. *capitis* strain AYP1020, complete genome (Year: 2015).*
Peter Hägg et al., "A host/plasmid system that is not dependent on antibiotics and antibiotic resistance genes for stable plasmid maintenance in *Escherichia coli*", Journal of Biotechnology 111 (2004) 17-30, Jul. 1, 2004.
Esteban Martínez-Garciía et al., "Mining Environmental Plasmids for Synthetic Biology Parts and Devices", Plasmids-Biology and Impact in Biotechnology and Discovery, Chapter 32, pp. 633-649 (2015), Feb. 2015.

(Continued)

*Primary Examiner* — Celine X Qian
*Assistant Examiner* — Tiffany Nicole Grooms
(74) *Attorney, Agent, or Firm* — LEX IP MEISTER, PLLC

(57) ABSTRACT

The present invention relates to a gene expression cassette including a synthetic 5' untranslated region (5' UTR), a promoter, and a regulatory gene; a recombinant vector including a replication origin and the gene expression cassette; a recombinant microorganism which has the recombinant vector introduced thereinto and shows alleviated segregational instability and; a method for preparing a recombinant microorganism having alleviated segregational instability by introducing the recombinant vector thereinto; and a method for quantitatively controlling a plasmid copy number in a recombinant microorganism. According to the present invention, removal of infA and efp, which are genes indispensable for cells, encoding respectively for a translation initiation factor and a protein elongation factor (EF-P), from a microbial chromosome and introduction of the gene expression cassette including the regulatory gene with *Escherichia coli* serving as a host allow the stable maintenance of plasmids in an antibiotic-free medium without causing intercellular intrinsic variations. In addition, the precise control of expression levels of infA and efp in the recombinant microorganism by means of a promoter can lead to the quantitative control of PCN at high yield as well. Therefore, the present invention can find a broad spectrum of applications in a variety of industries producing recombinant proteins.

18 Claims, 8 Drawing Sheets
Specification includes a Sequence Listing.

(56) References Cited

OTHER PUBLICATIONS

Guillermo Rodrigo et al., "De novo automated design of small RNA circuits for engineering synthetic riboregulation in living cells", PNAS (2012) 109(38) 15271-15276, Sep. 18, 2012.
Hiroyuki Aoki et al., "The Gene Encoding the Elongation Factor P Protein Is Essential for Viability and Is Required for Protein Synthesis", The Journal of Biological Chemistry (1997) 272(51) 32254-32259, Dec. 19, 1997.
Martinez-Garcia, Esteban et al., "Mining Environmental Plasmids for Synthetic Biology Parts and Devices", Plasmids-Biology and Impact in Biotechnology and Discovery, Edited by Tolmasky, Marcelo E. et aL American Society for Microbiology, 2015, Chapter 32. pp. 633-649.
NCBI GenBank: KX353597. I: Synthetic Plasmid pTig-PhiF, complete sequence (Nov. 7, 2016).
NCBI GenBank: KM23432 I .1: Boolean Integrase Logic Vector NAND Gate BCD-RFP, complete sequence (Jun. 8, 2015).
Seselvamani, Ram Shankar Velm et al., "Antibiotic-free Segregational Plasmid S1abihzation m *Escherichia coli* owing to the Knockou1 or Triosephosphate Isomerase (1piA).", Microbial Cell Factories, 2014, vol. 13, Article No. 58. inner pp. 1-13.
Zhou, S. et aL "Obtaining a Panel of Cascade Promoter-5'-UTR Complexes in *Escherichia coli*", ACS Synthetic Biology. 20 1 7 (Publication date: Mar. 2, 2017), vol. 6, pp. 1065-1107 5.
Kanoria Shaveta et al., "A 28 nt Long Synthetic 5'UTR (synJ) as an Enhancer of Transgene Expression in Dicotyledonous Plan1s", BMC Biotechnology, 20J 2, vol. 12. Article No. 85, inner pp. 1-14.
PCT/KR2018/004038, International Search Report and Written Opinion, with English translation, mailed Jul. 30, 2018, 15 pages.
Hágg, P., et al. "A host/plasmid system that is not dependent on antibiotics and antibiotic resistance genes for stable plasmid maintenance in *Escherichia coli*", Journal of Biotechnology 111, pp. 17-30, 2004.
Rodrigo, G., et al. "De novo automated design of small RNA circuits for engineering synthetic riboregulation in living cells", PNAS, vol. 109, No. 38, pp. 15271-15276, Sep. 18, 2012.
Aoki, H., et al. "The Gene Encoding the Elongation Factor P Protein Is Essential for Viability and Is Required for Protein Synthesis", vol. 272, No. 51, pp. 32254-32259, Dec. 19, 1997.

\* cited by examiner

[FIG. 1]
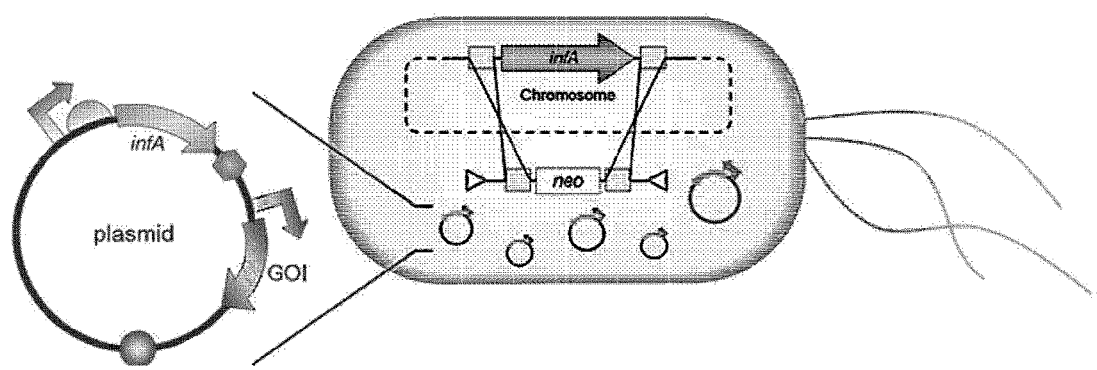
[FIG. 2]
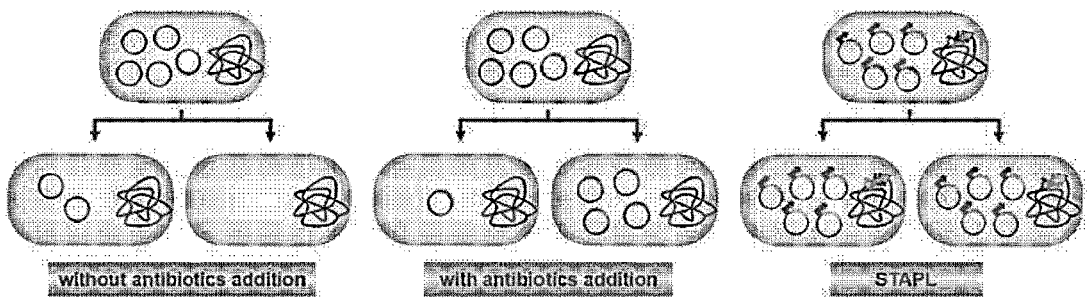

[FIG. 3]
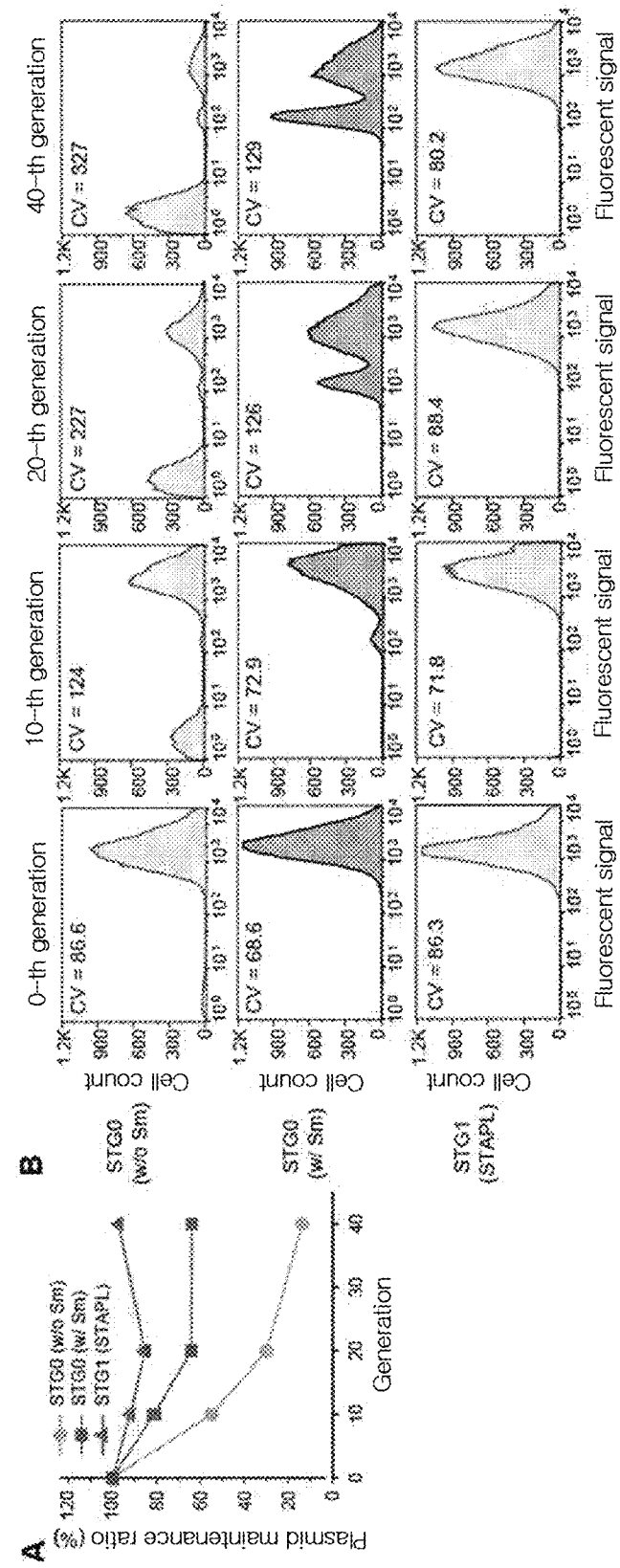

[FIG. 4]
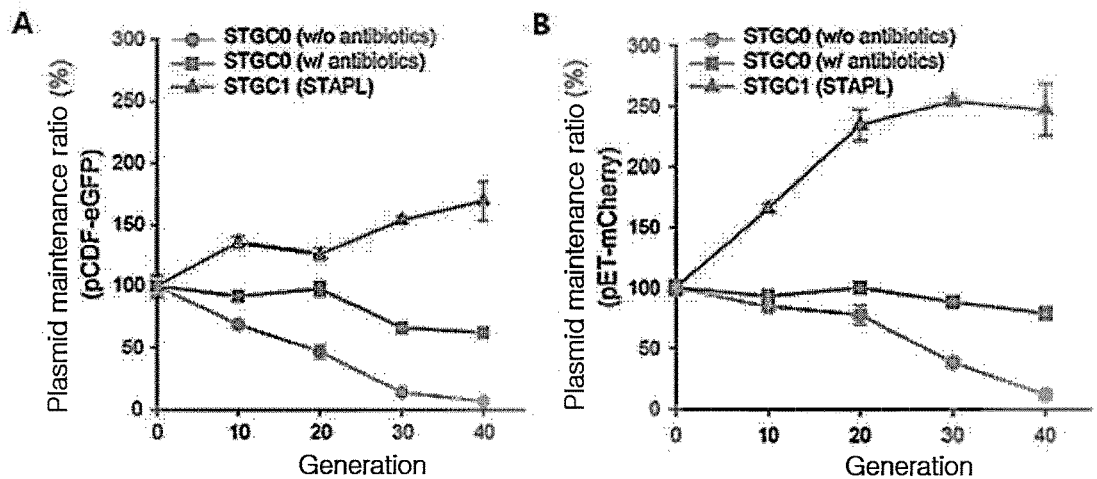
[FIG. 5]
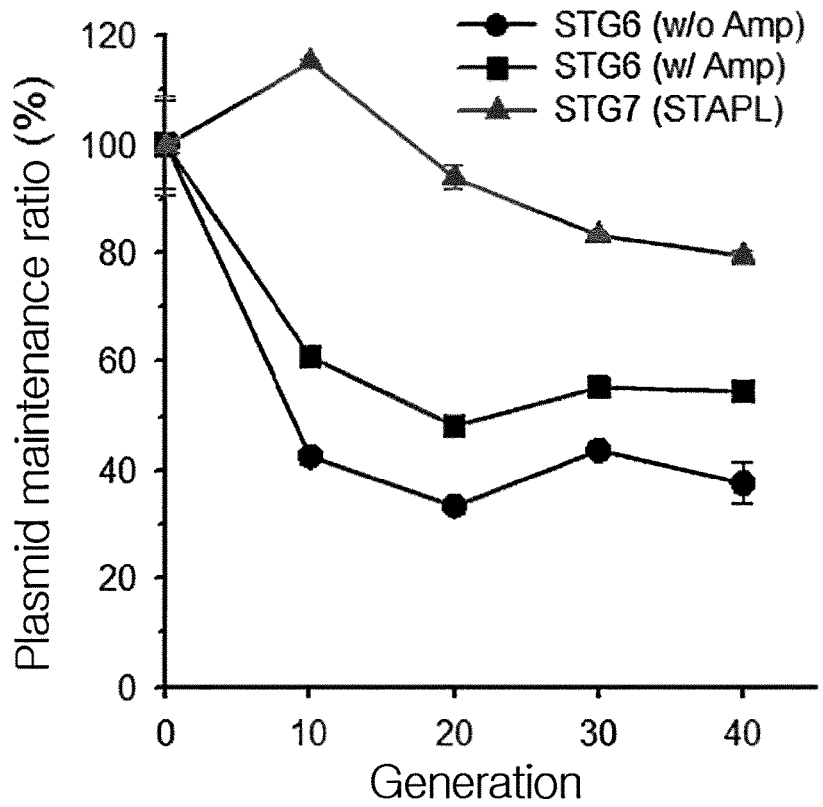

[FIG. 6]
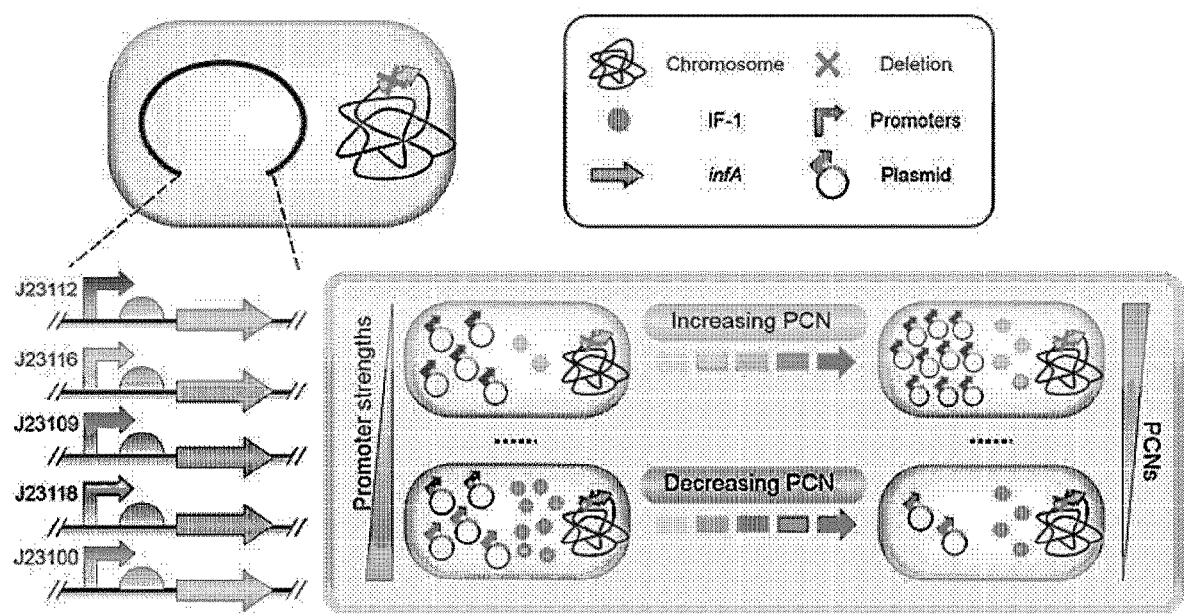

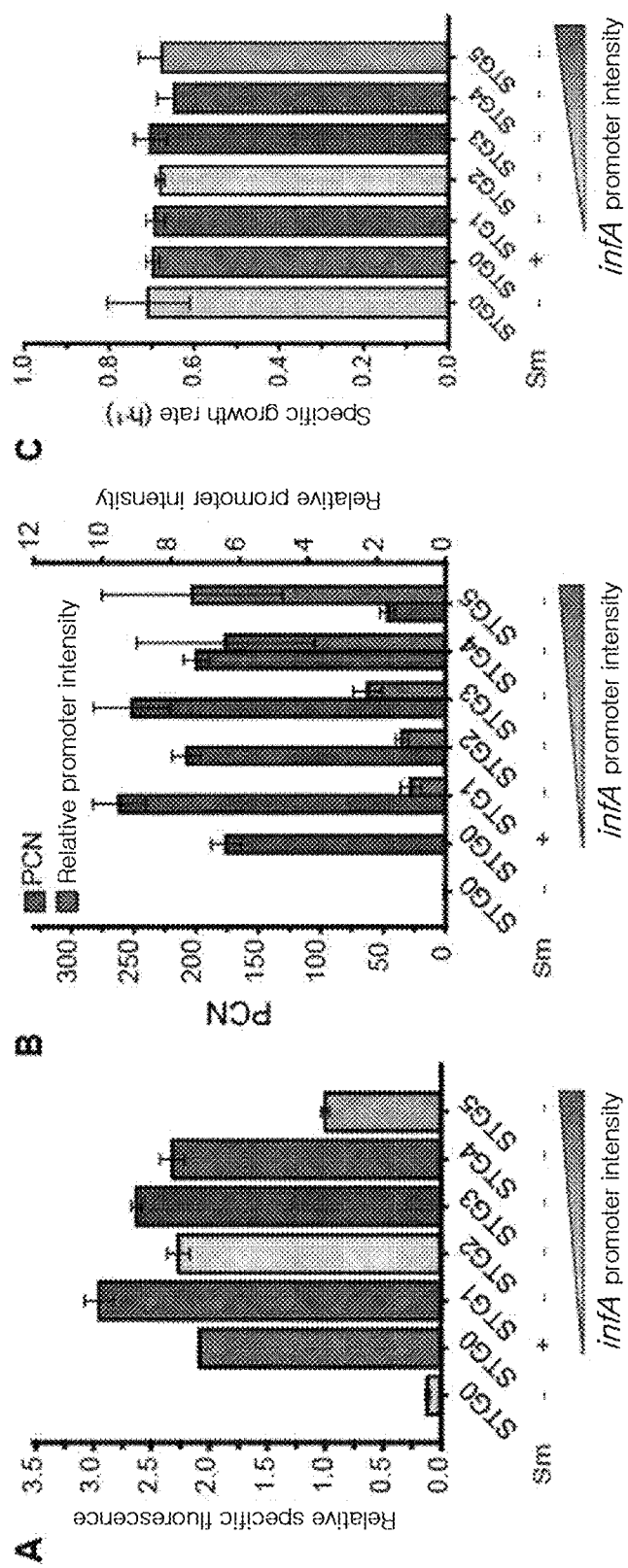
[FIG. 7]

[FIG. 8]
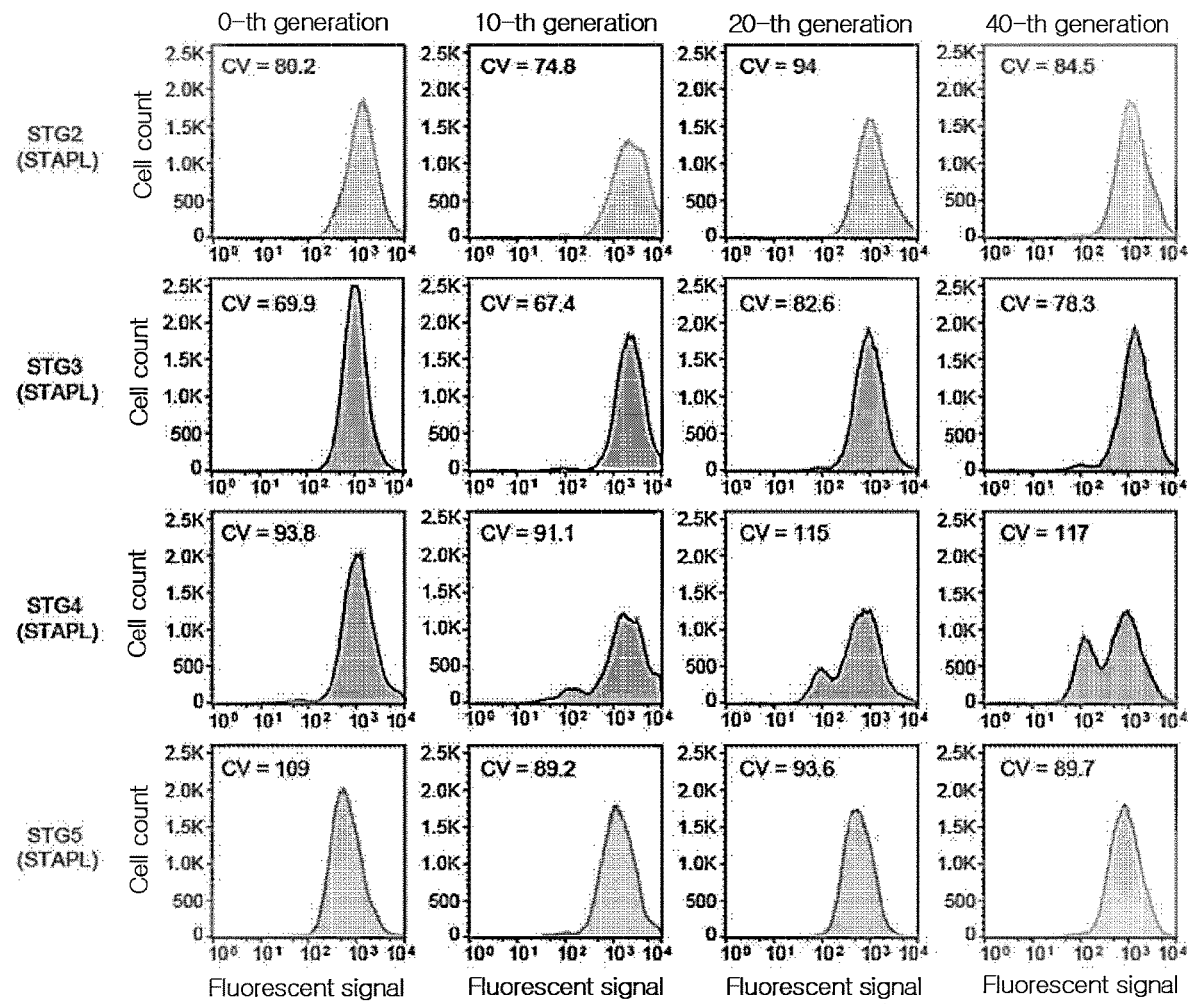

[FIG. 9]
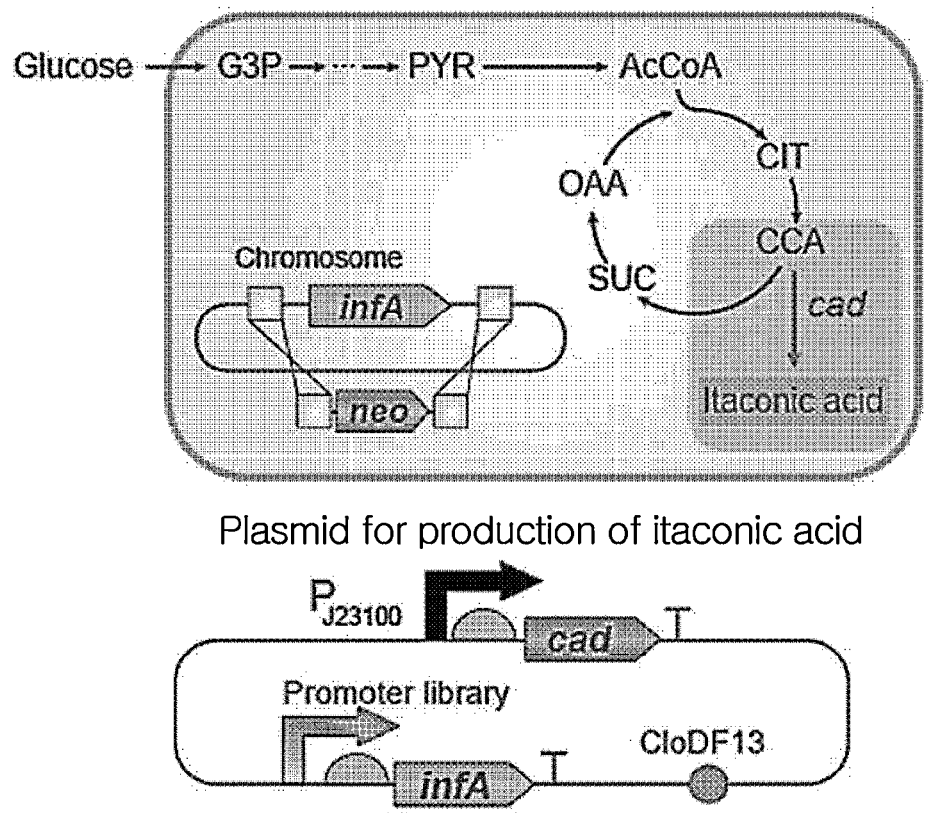
[FIG. 10]
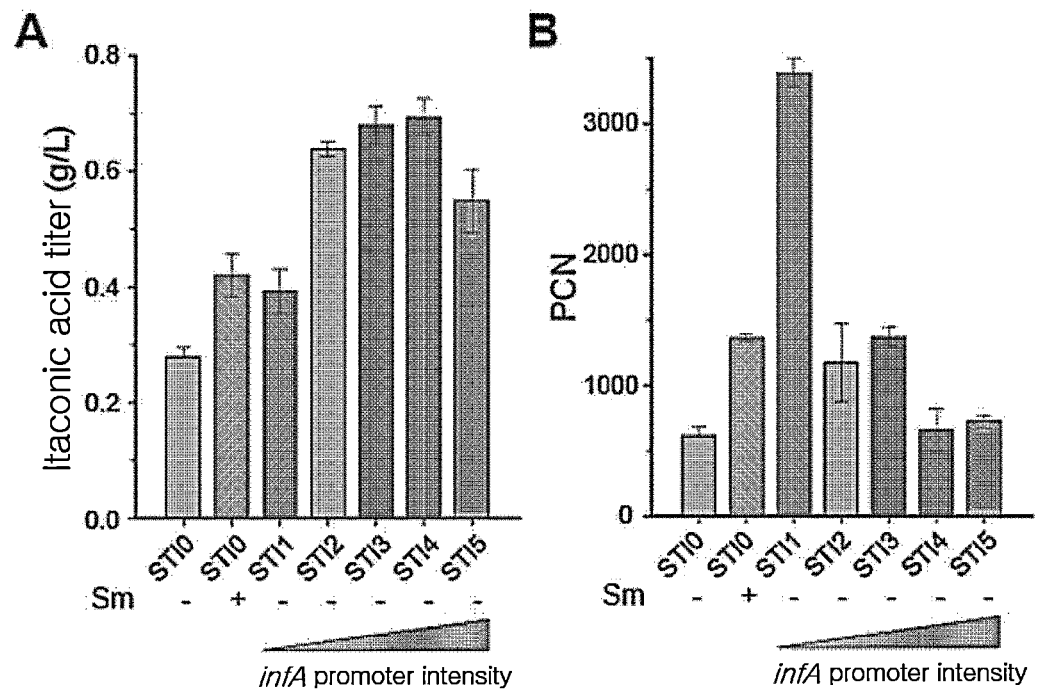

[FIG. 11]
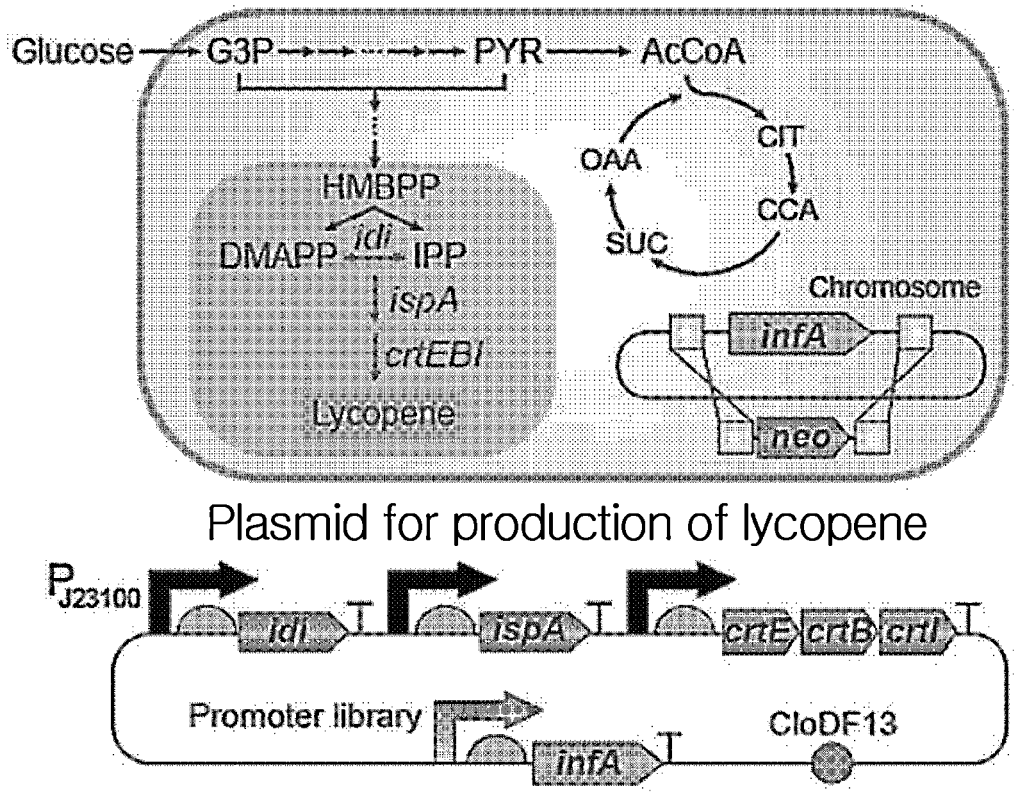
[FIG. 12]
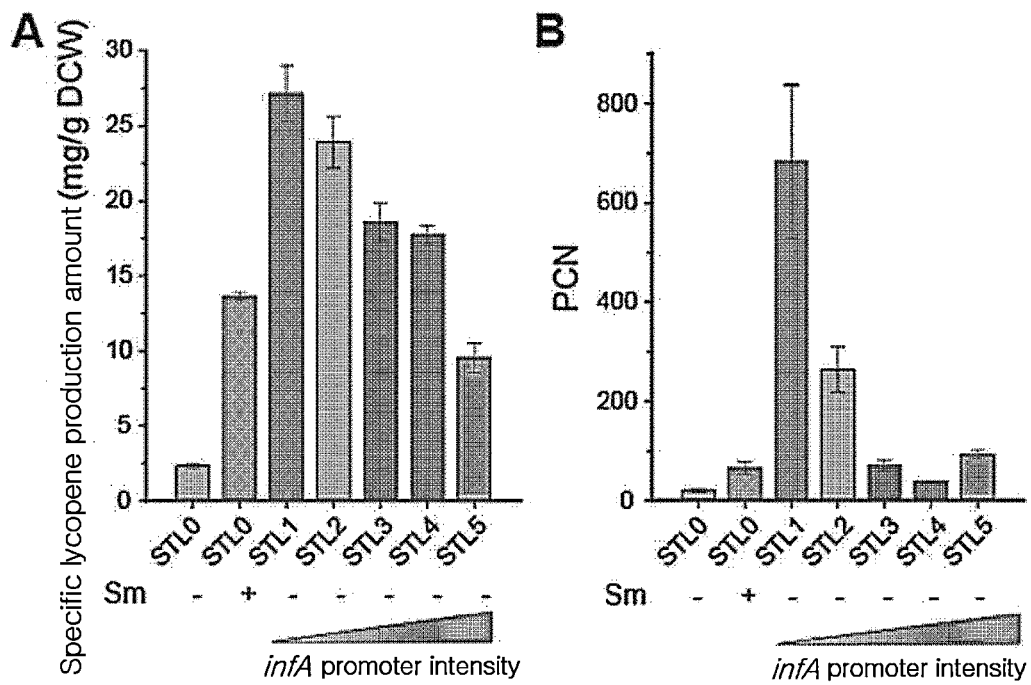

METHOD FOR QUANTITATIVELY CONTROLLING PLASMID COPY NUMBER IN ANTIBIOTIC-FREE PLASMID MAINTENANCE SYSTEM

REFERENCE TO AN ELECTRONIC SEQUENCE LISTING

The contents of the electronic sequence listing (103929560_1.TXT; Size: 24,522 bytes; and Date of Creation: Oct. 19, 2023) is herein incorporated by reference in its entirety. The contents of the electronic sequence listing in no way introduces new matter into the specification.

TECHNICAL FIELD

The present invention relates to a gene expression cassette including a synthetic 5' UTR (untranslated region), a promoter, and a regulatory gene: a recombinant vector including a replication origin and the gene expression cassette: a recombinant microorganism which has the recombinant vector introduced thereinto and shows alleviated segregational instability (segregational instability) and: a method for preparing a recombinant microorganism having alleviated segregational instability by introducing the recombinant vector thereinto; and a method for quantitatively controlling a plasmid copy number in a recombinant microorganism.

BACKGROUND ART

Plasmids were first discovered in the 1930s and is a typical carrier used to introduce genes into cells today in the field of biotechnology due to development of restriction enzymes. The plasmid is present in an independent manner in a cell, and it is easy to genetically manipulate the plasmid. The plasmid is small in size and thus, has high efficiency of introduction thereof into cells. Thus, the plasmid is applied to construct a long and complex genetic metabolic circuit necessary to produce exogenous protein. The greatest advantage of the plasmid which is not present in the chromosomes is that, at least, there is one copy of the plasmid or at most, 1000 copies thereof in a cell, and, thus, an amount of gene expression can be easily and broadly changed by a desired level. Thus, many studies utilizing gene overexpression have been conducted.

Plasmids may be present in cells continuously throughout generations by providing genes ability necessary for survival, such as antibiotic resistance to host cells in general. In this connection, if the cells are not chemically treated with antibiotics, the plasmid is naturally excluded from the host cell since it is only a parasite that does not benefit the host cell. When cell division occurs, a subpopulation with fewer plasmids occurs due to segregational instability (segregational instability). Thus, the subpopulation has a less metabolic burden to maintain the plasmid, influence of the subpopulation on the medium increases to reduce production performance. Therefore, it is essential to use antibiotics to keep the plasmid remaining in the cell. However, the user is reluctant to use antibiotics because they are expensive, pollute an end product, and have the potential to create multi-drug resistance organisms (multi-drug resistance organism). Furthermore, since the antibiotics are degraded by antibiotic resistance proteins during prolonged incubation thereof, the antibiotics are not suitable for the stable maintenance of the plasmids. For this reason, a new strategy is needed to keep plasmids stable in cells without the need for antibiotics.

In an alternative to solving the segregational instability of plasmids without the use of antibiotics, an antibiotic-free plasmid system (antibiotic-free plasmid system) has been developed since the 1980s. Examples of these systems include the essential gene complementation system (essential gene complementation system), toxin-antitoxin system (toxin-antitoxin system), operator-repressor titration system (operator-repressor titration system), RNA-based selection marker system (RNA-based selection marker system), and the like. Among these, the essential gene complementary system is a system that maintains the plasmid by expressing the essential gene in the plasmid rather than removing the essential gene of chromosome. Generally, there are many essential genes that may be used in this system. Further, this system has no off-target effect and no cytotoxicity. Thus, this system is most preferred among the systems. Previous studies from the 1990s have applied the essential gene complementary system to various host organisms while targeting essential genes involved primary metabolites, reducing cofactors, protein and cell wall synthesis.

The plasmid copy number (plasmid copy number, PCN) determines the expression level of the entire gene in the plasmid, in an independent manner of the 5'-UTR (5'-untranslated region) intensity or the promoter of the gene. The ability to regulate the PCN makes it possible to regulate the expression levels of target genes and metabolic pathways. Therefore, the PCN plays a very important role in the industrial mass production of bio-based compounds. In the field of metabolic engineering, different replication origins with various PCNs have been used as a tool to balance multiple gene pathways. However, the PCN of a commonly used plasmid has a very wide range and the PCN has a large intercellular variation. Thus, even with the same culture conditions, the balancing results are inconsistent due to the large intercellular variation of the PCN. Further, all of the PCN regulatory systems developed so far need antibiotics. Studies that control copy numbers using rational approaches such as random mutations have the disadvantage that it is difficult to analyze the pattern and difficult to fine-tune the pattern. Further, the expensive antibiotic must be added to the medium. Thus, there is a need for a system capable of stably controlling the plasmid copy number in an antibiotic-free medium.

DISCLOSURE

Technical Problem

Therefore, the present inventors have been studying a system capable of regulating the plasmid copy number in the antibiotic-free medium. In this study, we confirmed that when using, as a regulatory gene, infA and efp which are essential regulatory genes for survival, and precisely regulating an expression level of the gene using a promoter, the PCN was quantitatively controlled in a predictable manner. We named the present system as STAPL (Stable and Tunable PLasmid) and completed the present invention.

Thus, a purpose of the present invention is to provide a gene expression cassette including a synthetic 5' UTR (untranslated region), a promoter, and a regulatory gene: a recombinant vector including a replication origin and the gene expression cassette: a recombinant microorganism which has the recombinant vector introduced thereinto and shows alleviated segregational instability and: a method for preparing a recombinant microorganism having alleviated segregational instability (segregational instability) by introducing the recombinant vector thereinto; and a method for quantitatively controlling a plasmid copy number in a recombinant microorganism.

Technical Solution

To achieve the purpose, the present invention provides a gene expression cassette containing a synthetic 5' UTR (untranslated region), a promoter, and a regulatory gene.

Further, the present invention provides a recombinant vector containing a replication origin and the gene expression cassette.

Further, the present invention provides a recombinant microorganism with alleviated segregational instability (segregational instability) which has the recombinant vector introduced thereto.

Further, the present invention provides a method for preparing the recombinant microorganism having alleviated segregational instability (segregational instability), in which the method includes introducing the recombinant vector thereto.

Further, the present invention provides a method for quantitatively controlling a plasmid copy number in a recombinant microorganism, in which the method includes: (a) a step of selecting a promoter having a target transcription amount based on a target plasmid copy number: (b) a step of producing a gene expression cassette including a promoter selected in the step (a), a synthetic 5'UTR, and at least one regulatory gene selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, sec, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, rne, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, yejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, yqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, vidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, orn, yjeE, rpsR, ppa, valS, yjgP, yjgQ, dnaC and dnaT: and (c) a step of introducing the gene expression cassette produced in the step (b) into the microorganism.

Advantageous Effects

According to the present invention, infA as a gene for encoding a translation initiation factor essential for a cell, and efp for encoding a protein elongation factor (EF-P) are removed from a chromosome of the microorganism. Then, the gene expression cassette containing the regulatory gene is introduced using *Escherichia coli* as a host. Thus, the plasmids can be stably maintained in the antibiotic-free medium without intracellular intrinsic mutations. Further, when the expression level of infA and efp in the recombinant microorganism is precisely controlled using the promoter, the PCN may be quantitatively controlled at high efficiency. Thus, the present system may be widely applied in various industries for producing recombinant proteins.

DESCRIPTION OF DRAWINGS

FIG. 1 is a schematic diagram of an STG1 strain to which a STAPL is applied, where a recombinant vector containing a gene expression cassette according to the present invention has been introduced into a wild-type *Escherichia coli* W3110 strain.

FIG. 2 is a schematic diagram showing conventional plasmid segregational instabilities with and without application of antibiotics, and a process in which a plasmid is stably maintained in the strain to which STAPL is applied according to the present invention.

FIG. 3 shows measurement results of plasmid maintenance ratios for a STG1 containing the recombinant vector according to the present invention and STG0 *E. coli* strain without the STAPL application thereto subjected to culturing for 40 generations (FIG. 3A), and shows a fluorescence profile versus the number of cells for the STG1 containing the recombinant vector according to the present invention and STG0 *E. coli* strain without the STAPL application thereto subjected to culturing for each of 0, 10, 20, and 40 generations (FIG. 3B).

FIG. 4 shows fluorescence measurement results using eGFP (FIG. 4A) or mCherry (FIG. 4B) of plasmid maintenance ratios for a STGC1 strain transformed by introducing thereto two plasmids containing infA and efp, respectively, that is, subjected to the STAPL treatment, for STGC0 strains not subjected to the STAPL treatment, as subjected to culturing for 40 generations.

FIG. 5 shows a plasmid maintenance ratio for STG7 containing a high copy number of recombinant plasmids according to the present invention and STG6 *E. coli* strain without STAPL application thereto, as cultured for 40 generations.

FIG. 6 is a schematic diagram of a mechanism of PCN regulation using a control mechanism of expression amount of infA in a STAPL treated strain according to the present invention.

FIG. 7 shows a relative specific fluorescence (FIG. 7A), an actual PCN and a relative promoter intensity of infA (FIG. 7B), and a strain-specific growth rate (FIG. 7C) for STG1-5 strains cultured in an antibiotic-free medium, in which the STG1-5 strains are produced by applying STAPL system to an STG0 strain and introducing thereto gene expression cassettes including, as a promoter, infA of various intensities.

FIG. 8 shows a fluorescence profile versus the number of cells for STG2-5 strains according to the present invention subjected to culturing for each of 0, 10, 20, and 40 generations.

FIG. 9 is a schematic diagram showing a STAPL system containing a cad gene as a target gene for production of itaconic acid and a corresponding plasmid.

FIG. 10 shows results (FIG. 10A) at 30 hours after production of itaconic acid using a recombinant strains STI0-5 according to the present invention and a corresponding PCN (FIG. 10B).

FIG. 11 is a schematic diagram showing a STAPL system containing idi, ispA, and crtEBI genes as target genes for lycopene production and a corresponding plasmid.

FIG. 12 shows a specific aspect of lycopene production (FIG. 12A) and a corresponding PCN (FIG. 12B) when OD of a strain for the lycopene production using recombinant strains STL0-5 according to the present invention is about 0.8.

MODES OF THE INVENTION

The present invention provides a gene expression cassette containing a synthetic 5' UTR (untranslated region), a promoter and a regulatory gene.

Hereinafter, the present invention will be described in detail.

As used herein, a term "regulatory gene" refers to an essential gene for survival that is directly related to viability of a host cell. When the regulatory gene is expressed in a plasmid rather than a host cell chromosome, the essential gene for survival that is essential for survival of the host cell can be expressed in the plasmid. Thus, a transcription level of the plasmid can be regulated using a mechanism of regulating an expression amount of the essential gene for survival.

The gene expression cassette according to the present invention may employ a gene known as an essential gene in E. coli as the regulatory gene. Preferably, the regulatory gene may be at least one regulatory gene selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, secD, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, me, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, yejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, yqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, yidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, orn, yjeE, rpsR, ppa, valS, yjgP, yjgQ, dnaC and dnaT. More preferably, the regulatory gene may include infA and efp.

As used herein, a term "promoter" is involved in binding of RNA polymerase to initiate transcription into a portion of DNA. Generally, the promoter refers to a sequence located upstream of and adjacent to a target gene and on a same strand as the target gene. In accordance with the present invention, the promoter may include a promoter synthesized to express the regulatory gene including at least one selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, secD, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, me, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, vejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, vqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, vidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, orn, yjeE, rpsR, ppa, valS, yjgP, yjgQ, dnaC and dnaT. The promoter is preferably a constitutive promoter. The constitutive promoter (constitutive promoter) means a promoter capable of expressing a gene at any time regardless of an external stimulus, a growth stage, or tissue characteristics. The constitutive promoter according to the present invention is used for the purpose of continuously inducing the expression of one or more regulatory genes selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, secD, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, me, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, yejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, vqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, vidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, om, yjeE, rpsR, ppa, valS, yjgP, yjgQ, dnaC and dnaT. Preferably, the constitutive promoter according to the present invention may include a promoter including a sequence set forth in SEQ ID NOS: 1 to 5. A sequence with at least 60%, preferably 70%, more preferably 80% or greater of a sequence homology with the above described sequence has a substantially homogenous function as the above described sequence and thus may be used as the constitutive promoter via appropriate addition, deletion, or substitution by the skilled person to the art. The constitutive promoter according to the present invention may preferably include, for example, J23112, J23116, J23109, J23118 and J23100 promoters, and the promoters may be purchased or synthesized. In accordance with the present invention, a degree of expression of the regulatory gene operably linked to the promoter can be selectively regulated by selecting the promoter having a desired expression intensity and using the selected promoter. This allows control of PCN, and production of a target gene.

The synthetic 5' UTR contained in the expression cassette according to the present invention is intended to down-regulate a gene. 5' UTR having a low intensity representing a predicted expression amount of 100 to 100,000 calculated from UTR Designer (doi: 10.1016/j.ymben.2012.10.006) may be used. Preferably, 5'UTR having a low intensity representing a predicted expression amount of 1000 to 2000 may be employed. In accordance with the present invention, one synthetic 5'UTR selected from a group consisting of base sequences represented by SEQ ID NOS: 54, 55, 56 and 59 may be used in a preferable example.

The gene expression cassette according to the present invention may further contain a target gene. The term "target gene" used herein refers to a gene for encoding a metabolite as a target product in a recombinant microorganism that incorporates the gene expression cassette according to the present invention. In accordance with the present invention, the target gene contained in the gene expression cassette may include a gene for encoding a substance required for mass production. In accordance with the present invention, genes for encoding itaconic acid or lycopene may be used, but the present invention is not limited thereto. The gene for encoding itaconic acid may be, but is not limited to, a cad foreign gene derived from *Aspergillus terreus*. Any sequence capable of achieving production of itaconic acid may be included in the sequence according to the present invention without any limitation. Further, the gene for encoding lycopene may be, but is not limited to, ispA and idi derived from *Escherichia coli* and crtEBI gene derived from *Pantoea agglomerans*. Any sequence capable of achieving the production of lycopene may be interpreted to be included in the sequences according to the present invention without any limitation.

The gene expression cassette according to the present invention may further include a terminator. The terminator contained in the gene expression cassette according to the present invention is linked to a terminal of the gene expression cassette DNA to terminate transcription of the gene expression cassette DNA. The terminator is not particularly limited and may be adopted and used appropriately by the person skilled in the art based on the promoter. In accordance with the present invention, in a preferred example, BBa_B1002 represented by SEQ ID NO: 53 was used.

Further, the present invention provides a recombinant vector containing a replication origin and the gene expression cassette.

As used herein, a term "vector" refers to a gene construct containing a base sequence operably linked to an appropriate regulatory sequence so that the target gene can be expressed in a suitable host. The regulatory sequence may include a promoter capable of initiating transcription, any operator sequence for regulating such transcription, and sequences that regulate termination of transcription and translation. The recombinant vector used in accordance with the present invention may be preferably a plasmid.

In accordance with the present invention, a plasmid may be used in an unrestricted manner regardless of an origin of the plasmid. Preferably, a plasmid containing a replication origin to allow the plasmid to have 1 to 600 copy numbers per cell may be used. More preferably, a plasmid containing a replication origin to allow the plasmid to have 40 to 500 copy numbers per cell may be used.

The recombinant vector according to the present invention contains a replication origin (replicon). As long as any sequence according to the present invention allows replication of the recombinant vector, the sequence may be used as the replication origin without any limitation. According to the present invention, in a preferred embodiment, when infA is used as the regulatory gene, CloDF-13 or PMB1 may be used as the replication origin. Alternatively, CloE1 may be used as the replicon when efp was used as the regulatory gene.

Further, the recombinant vector according to the present invention may include a promoter to regulate expression of the regulatory gene to allow the recombinant vector to be used as a cloning vector capable of regulating a copy number, and a restriction enzyme site for inserting the target gene. The recombinant vector according to the present invention may include a selection marker for selection of a cell with the recombinant vector.

Further, the present invention provides a recombinant microorganism with alleviated segregational instability (segregational instability) which has the recombinant vector introduced thereto.

As used herein, the phrase "alleviated segregational instability" means that a microorganism into which a recombinant vector has been introduced can stably maintain the number of recombinant vectors above a certain number within a strain in a series of subcultures.

According to the present invention, a wild-type *E. coli* W3110 strain may be used as a preferred example of the recombinant microorganism. However, the present invention is not limited thereto. As used herein, the wild-type *Escherichia coli* refers to a natural form of *Escherichia coli* that has not been subjected to artificial gene recombination, substitution, or mutation.

The recombinant microorganism according to the present invention may be characterized in that one or more regulatory genes selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, secD, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, rne, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, vejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, vqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, yidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, om, yjeE, rpsR, ppa, valS, yjgP, yjgQ, dnaC and dnaT on chromosomes in the recombinant microorganism are removed in order to solve the segregational instability and to quantitatively regulate the number of the recombinant vectors, more preferably, the plasmid copy number, using the gene cassette introduced thereto. Preferably, one or more regulatory genes selected from a group consisting of infA and efp may be removed.

Further, the present invention provides a method for preparing the recombinant microorganism having alleviated segregational instability (segregational instability), in which the method includes a step of introducing the recombinant vector thereto.

Using the recombinant microorganism production method according to the present invention, the segregational instability can be alleviated, and the recombinant microorganisms can be produced in which the number of recombinant vectors, more preferably the plasmid copy number is quantitatively regulated using the gene cassette introduced thereto.

Further, the present invention provides a method for quantitatively controlling a plasmid copy number in a recombinant microorganism, in which the method includes: (a) a step of selecting a promoter having a target transcription amount based on a target plasmid copy number: (b) a step of producing a gene expression cassette including a promoter selected in the step (a), a synthetic 5′UTR, and at least one regulatory gene selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, sec, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, rne, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, vejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, yqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, vidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, or, yjeE, rpsR, ppa, valS, yjgP, yjgQ, dnaC and dnaT: and (c) a step of introducing the gene expression cassette produced in the step (b) into the microorganism.

In the method for quantitatively controlling a plasmid copy number in a recombinant microorganism in accordance with the present invention, it is possible to quantitatively control the plasmid copy number by selecting the promoter having the target transcription amount according to the target plasmid copy number. When the promoter having a high intensity is selected in the step (a), the plasmid copy number in the recombinant microorganism can be kept smaller. To the contrary, when selecting the promoter with a low intensity, the plasmid copy number in the recombinant microorganism can be maintained larger. Therefore, in order to control the plasmid copy number in the recombinant microorganism to the desired amount, the plasmid copy number in the recombinant microorganism may be quantitatively controlled by selecting the promoter having the target transcription amount and introducing the selected promoter into the recombinant vector.

In the method for quantitatively controlling a plasmid copy number in a recombinant microorganism in accordance with the present invention, the gene expression cassette introduced into the recombinant microorganism may further include the target gene or the terminator. Preferably, the promoter according to the present invention contained in the gene expression cassette may include a promoter including a sequence set forth in SEQ ID NOS: 1 to 5. A sequence with at least 60%, preferably 70%, more preferably 80% or greater of a sequence homology with the above described sequence has a substantially homogenous function as the above described sequence and thus may be used as the promoter via appropriate addition, deletion, or substitution by the skilled person to the art. The constitutive promoter according to the present invention may preferably include one promoter (J23112, J23116, J23109, J23118 and J23100) selected from a group consisting of promoters represented by SEQ ID NOS: 1 to 5. The promoters may be purchased or synthesized.

The method for quantitatively controlling a plasmid copy number in a recombinant microorganism in accordance with the present invention may be characterized in that one or more regulatory genes selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, sec, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, me, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, yejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, vqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, vidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, om, yjeE, rpsR, ppa, valS, yjgP, yjgQ, dnaC and dnaT on chromosomes in the recombinant microorganism may be removed. When the regulatory gene is removed from the chromosome in the microorganism and expressed in the plasmid, the essential gene for survival which is essential for survival of the host cell may be expressed in the plasmid. Thus, the plasmid transcription level is regulated via regulation mechanism of an expression amount of the essential gene for survival, thereby allowing quantitative regulation of the plasmid copy number in the recombinant microorganism.

When using the method to quantitatively control the plasmid copy number in the recombinant microorganism according to the present invention, it is possible to control the plasmid copy number in a stable manner when the culturing is carried out in a medium without antibiotics.

In the method for quantitatively controlling the plasmid copy number in a recombinant microorganism according to the present invention, regulation of the plasmid copy number can be controlled based on the intensity of the selected promoter. When the promoter having a high intensity is selected, the plasmid copy number in the recombinant microorganism can be kept smaller. To the contrary, when selecting the promoter with a low intensity, the plasmid copy number in the recombinant microorganism can be maintained larger. Therefore, in order to control the plasmid copy number in the recombinant microorganism to the desired amount, the plasmid copy number in the recombinant microorganism may be quantitatively controlled by selecting the promoter having the target intensity and introducing the selected promoter into the recombinant vector.

The present invention will be described in detail with reference to the following Examples. These Examples are merely illustrative of the invention and are not intended to limit the scope according to the present invention.

Strain and Plasmid as Used

Following Table 1 summarizes the strain and plasmid as used in the following examples.

TABLE 1

| Name | Related feature | Source |
|---|---|---|
| Strain | | |
| Mach-T1$^R$ | E. coli F$^{-\Phi}$80(lacZ)ΔM15 ΔlacX74 hsdR($r_K^-$mK+) ΔrecA1398 endA1tonA | Invitrogen |
| W3110 | E. coli F$^-\lambda^-$rph-1IN(rrnD, rrnE)1 | ATCC27325 |
| STG0 | W3110/pCDF-eGFP | Present invention |
| STG1 | W3110 ΔinfA::Kan$^R$/pSTAPL_eGFPv1 | Present invention |
| STG2 | W3110 ΔinfA::Kan$^R$/pSTAPL_eGFPv2 | Present invention |
| STG3 | W3110 ΔinfA::Kan$^R$/pSTAPL_eGFPv3 | Present invention |
| STG4 | W3110 ΔinfA::Kan$^R$/pSTAPL_eGFPv4 | Present invention |
| STG5 | W3110 ΔinfA::Kan$^R$/pSTAPL_eGFPv5 | Present invention |
| STI0 | W3110/pCDF-CAD | Present invention |
| STI1 | W3110 ΔinfA::Kan$^R$/pSTAPL_CADv1 | Present invention |
| STI2 | W3110 ΔinfA::Kan$^R$/pSTAPL_CADv2 | Present invention |
| STI3 | W3110 ΔinfA::Kan$^R$/pSTAPL_CADv3 | Present invention |
| STI4 | W3110 ΔinfA::Kan$^R$/pSTAPL_CADv4 | Present invention |
| STI5 | W3110 ΔinfA::Kan$^R$/pSTAPL_CADv5 | Present invention |
| STL0 | W3110/pCDF_idi_ispA_crtEBI | Prior research |
| STL1 | W3110 ΔinfA::Kan$^R$/pSTAPL_LYCv1 | Present invention |
| STL2 | W3110 ΔinfA::Kan$^R$/pSTAPL_LYCv2 | Present invention |
| STL3 | W3110 ΔinfA::Kan$^R$/pSTAPL_LYCv3 | Present invention |
| STL4 | W3110 ΔinfA::Kan$^R$/pSTAPL_LYCv4 | Present invention |
| STL5 | W3110 ΔinfA::Kan$^R$/pSTAPL LYCv5 | Present invention |
| STGC0 | W3110 pCDF-eGFP/pET-mCherry | Present invention |
| STGC1 | W3110 ΔinfA | Present |

TABLE 1-continued

| Name | Related feature | Source |
|---|---|---|
| STG6 | Δefp::Kan$^R$/pSTAPL_eGFPv1/pSTAPL_mCherry W3110/pUC19-eGFP | Present invention |
| STG7 | W3110 ΔinfA::Kan$^R$/pSTAPL_eGFPv7 | Present invention |
| Plasmid | | |
| pKD46 | Red recombinase expression vector, Amp$^R$ | Prior research |
| pCDF_Duet | Expression vector, Sm$^R$, cloDF13ori | Novagen |
| pFRT72$_{variant}$ | T-vector containing kanamycin resistance gene | Prior research |
| pCDF-eGFP | pCDF_Duet/P$_{J23100}$-synUTR$_{egfp}$-egfp-T$_{BBa\_B1002}$ | Present invention |
| pSTAPL_eGFPv1 | pCDF_eGFP/P$_{J23116}$-synUTR$_{infA}$-infA-T$_{BBa\_B1002}$ | Present invention |
| pSTAPL_eGFPv2 | pCDF_eGFP/P$_{J23112}$-synUTR$_{infA}$-infA-T$_{BBa\_B1002}$ | Present invention |
| pSTAPL_eGFPv3 | pCDF_eGFP/P$_{J23109}$-synUTR$_{infA}$-infA-T$_{BBa\_B1002}$ | Present invention |
| pSTAPL_eGFPv4 | pCDF_eGFP/P$_{J23118}$-synUTR$_{infA}$-infA-T$_{BBa\_B1002}$ | Present invention |
| pSTAPL_eGFPv5 | pCDF_eGFP/P$_{J23100}$-synUTR$_{infA}$-infA-T$_{BBa\_B1002}$ | Present invention |
| pCDF-CAD | pCDF_Duet-P$_{tac}$-synUTR$_{cad}$-cad-T$_{T7}$ | Present invention |
| pSTAPL_CADv1 | pCDF-CAD/P$_{J23116}$-synUTR$_{infA}$-infA-T$_{BBa\_B1002}$ | Present invention |
| pSTAPL_CADv2 | pCDF-CAD/P$_{J23112}$-synUTR$_{infA}$-infA-T$_{BBa\_B1002}$ | Present invention |
| pSTAPL_CADv3 | pCDF-CAD/P$_{J23109}$-synUTR$_{infA}$-infA-T$_{BBa\_B1002}$ | Present invention |
| pSTAPL_CADv4 | pCDF-CAD/P$_{J23118}$-synUTR$_{infA}$-infA-T$_{BBa\_B1002}$ | Present invention |
| pSTAPL_CADv5 | pCDF-CAD/P$_{J23100}$-synUTR$_{infA}$-infA-T$_{BBa\_B1002}$ | Present invention |
| pCDF_idi_ispA_crtEBI | pCDF-Duet/P$_{J23100}$-idi-T$_{BBa\_B1005}$/P$_{J23100}$-ispA-T$_{BBa\_B1005}$/ P$_{J23100}$-crtE-crtB-crtI-T$_{BBa\_B1005}$ | Prior research |
| pSTAPL_LYCv1 | pCDF_idi_ispA_crtEBI/P$_{J23116}$-synUTR$_{infA}$-infA-T$_{BBa\_B1002}$ | Present invention |
| pSTAPL_LYCv2 | pCDF_idi_ispA_crtEBI/P$_{J23112}$-synUTR$_{infA}$-infA-T$_{BBa\_B1002}$ | Present invention |
| pSTAPL_LYCv3 | pCDF_idi_ispA_crtEBI/P$_{J23109}$-synUTR$_{infA}$-infA-T$_{BBa\_B1002}$ | Present invention |
| pSTAPL_LYCv4 | pCDF_idi_ispA_crtEBI/P$_{J23118}$-synUTR$_{infA}$-infA-T$_{BBa\_B1002}$ | Present invention |
| pSTAPL_LYCv5 | pCDF_idi_ispA_crtEBI/P$_{J23100}$-synUTR$_{infA}$-infA-T$_{BBa\_B1002}$ | Present invention |
| pCP20 | Flippase expression vector, Amp$^R$, Cm$^R$ | Prior research |
| pETDuet | Expression vector, Amp$^R$, pMB1ori | Novagen |
| pFRT2161 | T-vector containing kanamycin resistance gene | Present invention |
| pZ-mCherry | pZS21 plasmid containing mcherry gene | Prior research |
| pET-mCherry | pETDuet/P$_{J23100}$-synUTR$_{mcherry}$-mcherry-T$_{BBa\_B1002}$ | Present invention |
| pSTAPL_mCherry | pET-mCherry/P$_{J23116}$-synUTR$_{efp}$-efp-T$_{BBa\_B1002}$ | Present invention |

TABLE 1-continued

| Name | Related feature | Source |
|---|---|---|
| pUC19-eGFP | pUC19/P$_{J23118}$-synUTR$_{egfp}$-egfp-T$_{BBa\_B1002}$ | Present invention |
| pSTAPL_eGFPv7 | pUC19_eGFP/P$_{J23112}$-synUTR$_{infA}$-infA-T$_{BBa\_B1002}$ | Present invention |

Promoter and Primer Sequences as Used

Following Table 2 and Table 3 summarize promoter and primer sequences used in the following examples.

TABLE 2

| Promoter name | Sequence (5'-3') | Sequence in library* | Known relative intensity[†] | Actual measured relative intensity[‡,§,‖] | SED ID NO |
|---|---|---|---|---|---|
| J23112 | ctgatagctagctcagtc ctagggattatgctagc | 1 | 1 | 1.27 ± 0.20 | 1 |
| J23109 | tttacagctagctcagtc ctagggactgtgctagc | 4 | 106 | 2.26 ± 0.42 | 2 |
| J23116 | ttgacagctagctcagtc ctagggactatgctagc | 8 | 396 | 1.00 ± 0.30 | 3 |
| J23118 | ttgacggctagctcagtc ctaggtattgtgctagc | 14 | 1429 | 6.41 ± 2.60 | 4 |
| J23100 | ttgacggctagctcagtc ctaggtacagtgctagc | 19 | 2547 | 7.38 ± 2.64 | 5 |

*Sequences in the library represent an ascending sequence of 19 promoter intensities.
[†]The known relative intensities are based on fluorescence values (Registry of Standard Biological Parts, http://parts.igem.org/).
[‡]The actual measured relative intensities were determined by dividing the amount of infA transcript of STG1-5 strain by the respective PCNs.
[§]The actual measured relative intensity is normalized to the smallest value and the result is shown.
[‖]The difference between the known intensity of the promoter and the actually measured intensity of the promoter varies depending on the genetic background.

TABLE 3

| Primer name | Polynucleotide sequence (5'-3')*,[†,‡,§,‖] | SEQ ID NO |
|---|---|---|
| C-infA-F | gtggcgagtccatgttcagccg | 6 |
| C-infA-B | aaacctcatgggtggcaacggg | 7 |
| D-infA-F | tgccgaataatttctgggtaccacgatgcttgttttcaccacaagaatgagcatgac cggcgcgatgc | 8 |
| D-infA-B | ctcgttctttctcttcgcccatcaggcggtaaaacaatcagcgactacgggctcag cggatctcatgcgc | 9 |
| O-eGFP-F2 | gagagttcaGAGCTCTTGACGGCTAGCTCAGTCCTAGG TACAGTGCTAGC | 10 |
| O-eGFP-B | gcatgcggctGAGCTCGCGAAAAAACCCCGCCGAAGCG | 11 |
| O-infA-F2 | ctgaaaCCTCAGGTTTACAGCTAGCTCAGTCCTAGGG ACTGTGCTAGC | 12 |
| O-infA-B | CCTGAGGGCGAAAAAACCCCGCCGAAGCGGGGTTT TTTGCGtcagcgactacggaagacaatgcg | 13 |
| O-infA-F1v1 | ctgaaaCCTCAGGTTGACAGCTAGCTCAGTCCTAGG GACTATGCTAGCgtagtactggaaatgagcatcc | 14 |
| O-infA-F1v2 | ctgaaaCCTCAGGCTGATAGCTAGCTCAGTCCTAGG GATTATGCTAGCgtagtactggaaatgagcatcc | 15 |
| O-infA-F1v3 | ctgaaaCCTCAGGTTTACAGCTAGCTCAGTCCTAGGG ACTGTGCTAGCgtagtactggaaatgagcatcc | 16 |

TABLE 3-continued

| Primer name | Polynucleotide sequence (5'-3')*,†,‡,§,∥ | SEQ ID NO |
|---|---|---|
| O-infA-F1v4 | ctgaaaCCTCAGGTTGACGGCTAGCTCAGTCCTAGGT ATTGTGCTAGCgtagtactggaaatgagcatcc | 17 |
| O-infA-F1v5 | ctgaaaCCTCAGGTTGACGGCTAGCTCAGTCCTAGGT ACAGTGCTAGCgtagtactggaaatgagcatcc | 18 |
| O-eGFP-F1 | ctcagtcctaggtacagtgctagcatcctgcattaaaggagcatccattatggctag caagggcgagg | 19 |
| Q-pCDF-F | catgttagtcatgccccgc | 20 |
| Q-pCDF-B | ctcactcattaggcaccggg | 21 |
| Q-polA-F | gcgagcgatccagaagatct | 22 |
| Q-polA-B | gggtaaaggatgccacagaca | 23 |
| Q-infA-F | ggaaatgagcatccagtatggcc | 24 |
| Q-infA-B | gtagttttgcgcattttaccggag | 25 |
| O-cad-F1 | ggaattgtgagcggataacaattaaaaaaaacaaaaggagcatcacccatgacc aaacagagcgcagatagca | 26 |
| O-cad-F2 | catccaGGTCTCgggTTGACAATTAATCATCGGCTCGT ATAATGtgtggaattgtgagcggataacaattaaaaaaaa | 27 |
| O-cad-B1 | aaaaaaaaaccccgccgaagcggggtttttttttggtgcgatttaaaccagcggac ttttaaccggaca | 28 |
| O-cad-B2 | catccaGGTCTCgccaaaaaaaaaccccgccgaagcgg | 29 |
| O-pCDF-F | catccaGGTCTCgttggacctcaggcatttgagaagcacac | 30 |
| O-pCDF-B | catccaGGTCTCctcgaaccaggagtcgcataagggagagcgtc | 31 |
| C-efp-F | ggcacacgcagggcaaaaag | 32 |
| C-efp-B | ctggcagcgcgagagatgg | 33 |
| D-efp-F | gagggccttatggcaacgtactatagcaacgattttcgtgctggtcttaaaccgc atgaccgcgcgatgc | 34 |
| D-efp-B | ctctgacctgaataagtgatggtgcagcctgcaggccgcaccacaaccgccg cgacgacaggcacatgcg | 35 |
| O-mCherry-F1 | caggcgcgccGAGCTCTTGACGGCTAGCTCAGTCCTA GGTACAGTGCTAGCccctggattaaaagg | 36 |
| O-mCherry-F2 | TGCTAGCccctggattaaaaggagcatctttaatggtttccaagggcgag | 37 |
| O-mCherry-B | attcgaattcGAGCTCGCGAAAAAACCCCGCCGAAGCGG GGTTTTTTGCGtcattatttgtacagctcatccatgccac | 38 |
| O-efp-F1 | CTAGGGACTATGCTAGCtcctgattctcacataacccagaaaattat ggcaacgtactatagcaacg | 39 |
| O-efp-F2 | cgtcggtaccctcgagTTGACAGCTAGCTCAGTCCTAGGG ACTATGCTAGCtcctgattc | 40 |
| O-efp-B | ctttaccagactcgagGCGAAAAAACCCCGCCGAAGCGGGG TTTTTTGCGttacttcacgcgagagacgtattc | 41 |
| FRT2161_F | ccgcatgaccgcgcgatgcgaagttcctatactctctggagaataggaacttctca agatcccctcacgctgccgc | 42 |
| FRT2161_B | cgcgacgacaggcacatgcggaagttcctattctccagagagtataggaacttca gagcgcttttgaagctggggtgg | 43 |
| O-pUC19-F | tttgcgtgaaaCTCGAGcgccaagcttgcatgcctgc | 44 |
| O-pUC19-B | aggagtttacCCTGAGGggccagcaaaaggccaggaac | 45 |
| O-eGFP-F1v2 | TGCTAGCagggtgtgcgaaaggagcatctttaatggctagcaagggcgag g | 46 |

TABLE 3-continued

| Primer name | Polynucleotide sequence (5'-3')*,†,‡,§,‖ | SEQ ID NO |
|---|---|---|
| O-eGFP-F2v2 | tttgctgaaaCCTCAGGTTGACGGCTAGCTCAGTCCTAG GTATTGTGCTAGCagggtgtgcgaaaggag | 47 |
| O-eGFP-Bv2 | tagaccatttctcgag*GCGAAAAAACCCCGCC* | 48 |
| O-infA-F1v2 | GTCCTAGGGATTATGCTAGC*gtagtactggattttttgcatccagt atggccaaagaagacaatattg* | 49 |
| O-infA-F2v2 | cccgggtaccccccgggtaccGAGCTCCTGATAGCTAGCTCA GTCCTAGGGATTATGCTAGC*gtag* | 50 |
| O-infA-B1v2 | TCAGTGAGACCTCAGCGACTACGGAAGACAATG | 51 |
| O-infA-B2v2 | agtgccacctGACGTCGCGAAAAAACCCCGCCGAAGCGG GGTTTTTTGCG*tcagtgagacctcagcgactac* | 52 |

*The sequence of the italic style represents the corresponding gene sequence for recombination.
†The underlined lowercase letter sequence represents the 5'-UTR sequence.
‡The underlined uppercase letter sequences represent the promoter sequences.
§The uppercase letter indicates the restriction enzyme sequence.
‖The italic styled uppercase letter indicates the terminator sequence.

Plasmid Copy Number in STAPL System

Table 4 summarizes the plasmid copy numbers in the STAPL system measured in the following examples.

TABLE 4

| | | eGFP | | Itaconic acid | | Lycopene | |
|---|---|---|---|---|---|---|---|
| Promoter | Sm | Strain | PCN* | Strain | PCN* | Strain | PCN* |
| — | − | STG0 | 1 ± 0 | STI0 | 613 ± 74 | STL0 | 21 ± 3 |
| — | + | STG0 | 176 ± 12 | STI0 | 1365 ± 28 | STL0 | 65 ± 12 |
| J23116 | − | STG1 | 261 221 | STI1 | 3390 ± 105 | STL1 | 684 ± 155 |
| J23112 | − | STG2 | 208 ± 12 | STI2 | 1174 ± 305 | STL2 | 265 ± 43 |
| J23109 | − | STG3 | 251 ± 31 | STI3 | 1373 ± 73 | STL3 | 70 ± 11 |
| J23118 | − | STG4 | 200 ± 10 | STI4 | 663 ± 160 | STL4 | 38 ± 1 |
| J23100 | − | STG5 | 46 ± 6 | STI5 | 726 ± 46 | STL5 | 93 ± 9 |

*PCN was calculated by dividing the copy number of the chromosome by the copy number of the plasmid.

Terminator and 5'-UTR Sequences and Gene Sequences as Used

The terminator and 5'-UTR sequences and gene sequences used in the Example of the present invention are summarized in Table 5 below.

TABLE 5

| | | Nucletide sequence (5'-3') | SEQ ID NO |
|---|---|---|---|
| Terminator | BBa_1002 | cgcaaaaaaccccgcttcggcggggttttttcgc | 53 |
| 5'-UTR | infA(STG1-5) | gtagtactggaaatgagcatccagt | 54 |
| | infA(STG7) | gtagtactggattttttgcatccagt | 55 |
| | efp(STGC1) | tcctgattctcacataacccagaaaatt | 56 |
| | eGFP(STG0) | atcctgcattaaaggagcatccatt | 57 |
| | eGFP(STG6) | agggtgtgcgaaaggagcatcttta | 58 |
| | mCherry(STGC0) | ccctggattaaaaggagcatcttta | 59 |

TABLE 5-continued

| Gene | Nucletide sequence | SEQ ID NO |
|---|---|---|
| infA | atggccaaagaagacaatattgaaatgcaaggaaccgttcttgaaacgttgc ctaataccatgttccgcgtagagttagaaaacggtcacgtggttactgcacac atctccggtaaaatgcgcaaaaactacatccgcatcctgacgggcgacaaa gtgactgttgaactgaccccgtacgacctgagcaaaggccgcattgtcttcc gtagtcgctga | 60 |
| efp | atggcaacgtactatagcaacgattttcgtgctggtcttaaaatcatgttagac ggcgaaccttacgcggttgaagcgagtgaattcgtaaaaccgggtaaaggc caggcatttgctcgcgttaaaactgcgtcgtctgctgaccggtactcgcgtaga aaaaaccttcaaatctactgattccgctgaaggcgctgatgttgtcgatatgaa cctgacttacctgtacaacgacggtgagttctggcacttcatgaacaacgaaa cttttcgagcagctgtctgctgatgcaaaagcaattggtgacaacgctaaatgg ctgctggatcaggcagagtgtatcgtaactctgtggaatggtcagccgatctc cgttactccgccgaacttcgttgaactggaaatcgttgataccgatccgggcc tgaaaggtgataccgcaggtactggtggcaaaccggctaccctgtctactgg cgctgtggttaaagttccgctgtttgtacaaatcggcgaagtcatcaaagtgg atacccgctctggtgaatacgtctctcgcgtgaagtaa | 61 |
| eGFP | atggctagcaagggcgaggagctgttcaccggggtggtgcccatcctggtc gagctggacggcgacgtaaacggccacaagttcagcgtgtccggcgagg gcgagggcgatgccacctacggcaagctgaccctgaagttcatctgcacca ccggcaagctgcccgtgccctggcccaccctcgtgaccaccctgacctacg gcgtgcagtgcttcagccgctaccccgaccacatgaagcagcacgacttctt caagtccgccatgcccgaaggctacgtccaggagcgcaccatcttcttcaa ggacgacggcaactacaagacccgcgccgaggtgaagttcgagggcgac accctggtgaaccgcatcgagctgaagggcatcgacttcaaggaggacgg caacatcctggggcacaagctggagtacaactacaacagccacaacgtcta tatcatggccgacaagcagaagaacggcatcaaggtgaacttcaagatccg ccacaacatcgaggacggcagcgtgcagctcgccgaccactaccagcag aacacccccatcggcgacggccccgtgctgctgcccgacaaccactacct gagcacccagtccgccctgagcaaagaccccaacgagaagcgcgatcac atggtcctgctggagttcgtgaccgccgcgggatcactctcggcatggac gagctgtacaagtga | 62 |
| mCherry | atggtttccaagggcgaggaggataacatggctatcattaaagagttcatgc gcttcaaagttcacatggagggttctgttaacggtcacgagttcgagatcgaa ggcgaaggtgagggccgtccgtatgaaggcacccagaccgccaaactga agtgactaaaggcggcccgctgcctttttgcgtgggacatcctgagcccgc aatttatgtacggttctaaagcttatgttaaacacccagcggatatcccggact atctgaagctgtcttttccggaaggtttcaagtgggaacgcgtaatgaattttg aagatggtggtgtcgtgaccgtcactcaggactcctccctgcaggatggcg agttcatctataaagttaaactgcgtggtactaattttccatctgatggcccggt gatgcagaagaagacgatgggttgggaggcgtctagcaacgcatgtacc cggaagatggtgcgctgaaaggcgaaattaaacagcgcctgaaactgaaa gatggcggccattatgacgctgaagtgaaaaccacgtacaaagccaagaa acctgtgcagctgcctggcgcgtacaatgtgaatattaaactggacatcacct ctcataatgaagattatacgatcgtagagcaatatgagcgcgcggagggtcg tcattctaccggtggcatggatgagctgtacaaataa | 63 |
| codon optimized cad | CGGAAGAACGTCCGATTAGCAGCATTGCAGGT CAGATGAGCGTTGCATATATTCTGGCCGTTCA GCTGGTTGATCAGCAGTGTCTGCTGAGCCAGT TTAGCGAATTTGATGATAACCTGGAACGTCCG GAAGTTTGGGATCTGGCACGTAAAGTTACCAG CAGCCAGAGCGAAGAATTTGATCAGGATGGTA ATTGTCTGAGCGCAGGTCGTGTTCGTATTGAA TTTAATGATGGTTCCAGCATTACCGAAAGCGT TGAAAAACCGCTGGGTGTTAAAGAACCGATGC CGAATGAACGTATCCTGCATAAATATCGTACC CTGGCAGGTAGCGTTACCGATGAAAGCCGTGT GAAAGAAATTGAAGATCTGGTTCTGGGTCTGG ATCGTCTGACCGATATTAGTCCGCTGCTGGAA CTGCTGAACTGTCCGGTTAAAAGTCCGCTGGT TTAA | 64 |
| idi | ATGCAGACCGAACATGTGATTCTGCTGAACGC GCAGGGCGTGCCGACCGGCACCCTGGAAAAA TATGCGGCGCATACCGCGGATACCCGCCTGCA TCTGGCGTTTAGCAGCTGGCTGTTTAACGCGA AAGGCCAGCTGCTGGTGACCCGCCGCGCGCTG AGCAAAAAAGCGTGGCCGGGCGTGTGGACCA ACAGCGTGTGCGGCCATCCGCAGCTGGGCGAA AGCAACGAAGATGCGGTGATTCGCCGCTGCCG CTATGAACTGGGCGTGGAAATTACCCCGCCGG | 65 |

TABLE 5-continued

| | | SEQ ID NO |
|---|---|---|
| | AAAGCATTTATCCGGATTTTCGCTATCGCGCG ACCGATCCGAGCGGCATTGTGGAAAACGAAGT GTGCCCGGTGTTTGCGGCGCGCACCACCAGCG CGCTGCAGATTAACGATGATGAAGTGATGGAT TATCAGTGGTGCGATCTGGCGGATGTGCTGCA TGGCATTGATGCGACCCCGTGGGCGTTTAGCC CGTGGATGGTGATGCAGGCGACCAACCGCGA AGCGCGCAAACGCCTGAGCGCGTTTACCCAGC TGAAATAA | |
| ispA | ATGGATTTCCCGCAGCAGCTGGAAGCGTGTGT GAAACAGGCGAACCAGGCGCTGAGCCGCTTTA TTGCGCCGCTGCCGTTTCAGAACACCCCGGTG GTGGAAACCATGCAGTATGGCGCGCTGCTGGG CGGCAAACGCCTGCGCCCGTTTCTGGTGTATG CGACCGGCCACATGTTTGGCGTGAGCACCAAC ACCCTGGATGCGCCGGCGGCGGCGGTGGAATG CATTCATGCGTATAGCCTGATTCATGATGATCT GCCGGCGATGGATGATGATGATCTGCGCCGCG GCCTGCCGACCTGCCATGTGAAATTTGGCGAA GCGAACGCGATTCTGGCGGGCGATGCGCTGCA GACCCTGGCGTTTAGCATTCTGAGCGATGCGG ATATGCCGGAAGTGAGCGATCGCGATCGCATT AGCATGATTAGCGAACTGGCGAGCGCGAGCG GCATTGCGGGCATGTGCGGCGGCCAGGCGCTG GATCTGGATGCGGAAGGCAAACATGTGCCGCT GGATGCGCTGGAACGCATTCATCGCCATAAAA CCGGCGCGCTGATTCGCGCGGCGGTGCGCCTG GGCGCGCTGAGCGCGGGCGATAAAGGCCGCC GCGCGCTGCCGGTGCTGGATAAATATGCGGAA AGCATTGGCCTGGCGTTTCAGGTGCAGGATGA TATTCTGGATGTGGTGGGCGATACCGCGACCC TGGGCAAACGCCAGGGCGCGGATCAGCAGCT GGGCAAAAGCACCTATCCGGCGCTGCTGGGCC TGGAACAGGCGCGCAAAAAAGCGCGCGATCT GATTGATGATGCGCGCCAGAGCCTGAAACAGC TGGCGGAACAGAGCCTGGATACCAGCGCGCTG GAAGCGCTGGCGGATTATATTATTCAGCGCAA CAAATAA | 66 |
| crtE | ATGGTATCTGGCTCAAAGGCTGGCGTCTCGCC ACATCGCGAAATTGAAGTGATGCGCCAGAGCA TTGATGATCATCTGGCGGGCCTGCTGCCGGAA ACCGATAGCCAGGATATTGTGAGCCTGGCGAT GCGCGAAGGCGTGATGGCGCCGGGCAAACGC ATTCGCCCGCTGCTGATGCTGCTGGCGGCGCG CGATCTGCGCTATCAGGGCAGTATGCCGACCC TGCTGGATCTGGCGTGCGCGGTGGAACTGACC CATACCGCGAGCCTGATGCTGGATGATATGCC GTGCATGGATAACGCGGAACTGCGCCGCGGCC AGCCGACCACCCATAAAAAATTTGGCGAAAGC GTGGCGATTCTGGCGAGCGTGGGCCTGCTGAG CAAAGCGTTTGGCCTGATTGCGGCGACCGGCG ATCTGCCGGGCGAACGCCGCGCGCAGGCGGTG AACGAACTGAGCACCGCGGTGGGCGTGCAGG GCCTGGTGCTGGGCCAGTTTCGCGATCTGAAC GATGCGGCGCTGGATCGCACCCCGGATGCGAT TCTGAGCACCAACCATCTGAAAACCGGCATTC TGTTTAGCGCGATGCTGCAGATTGTGGCGATT GCGAGCGCGAGCAGCCCGAGCACCCGCGAAA CCCTGCACGCGTTTGCGCTGGATTTTGGCCAG GCGTTTCAGCTGCTGGATGATCTGCGCGATGA TCATCCGGAAACCGGCAAAGATCGCAACAAA GATGCGGGCAAAAGCACCCTGGTGAACCGCCT GGGCGCGGATGCGGCGCGCCAGAAACTGCGC GAACATATTGATAGCGCGGATAAACATCTGAC CTTTGCGTGCCCGCAGGGCGGCGCGATTCGCC AGTTTATGCATCTGTGGTTTGGCCATCATCTGG CGGATTGGAGCCCGGTGATGAAAATTGCGTAA | 67 |
| crtB | ATGTCCCAACCCCCCTTGCTAGACCACGCAAC CCAGACGATGGCGAACGGCAGCAAGAGCTTT GCGACCGCGGCGAAACTGTTTGATCCGGCGAC CCGCCGCAGCGTGCTGATGCTGTATACCTGGT GCCGCCATTGCGATGATGTGATTGATGATCAG ACGCATGGCTTTGCGAGCGAAGCGGCGGCGG | 68 |

TABLE 5-continued

|  | SEQ ID NO |
|---|---|
| AAGAAGAAGCGACCCAGCGCCTGGCGCGCCT<br>GCGCACCCTGACCCTGGCGGCGTTTGAAGGCG<br>CGGAAATGCAGGACCCGGCGTTTGCGGCGTTT<br>CAGGAAGTGGCGCTGACCCACGGCATTACCCC<br>GCGCATGGCGCTGGATCATCTGGATGGCTTTG<br>CGATGGATGTGGCGCAGACCCGCTATGTGACC<br>TTTGAAGATACCCTGCGCTATTGCTATCATGTG<br>GCGGGCGTGGTGGGCCTGATGATGGCGCGCGT<br>GATGGGCGTGCGCGATGAACGCGTGCTGGATC<br>GCGCGTGCGATCTGGGCCTGGCGTTTCAGCTG<br>ACCAACATTGCGCGCGATATTATTGATGATGC<br>GGCGATTGATCGCTGCTATCTGCCGGCGGAAT<br>GGCTGCAGGATGCGGGCCTGACCCCGGAAAA<br>CTATGCGGCGCGCGAAAACCGCGCGGCGCTGG<br>CGCGCGTGGCGGAACGCCTGATTGATGCGGCG<br>GAACCGTATTATATTAGCAGCCAGGCGGGCCT<br>GCATGATCTGCCGCCGCGCTGCGCGTGGGCGA<br>TTGCGACCGCGCGCAGCGTGTATCGCGAAATT<br>GGCATTAAAGTGAAAGCGGCGGGCGGCAGCG<br>CGTGGGATCGCCGCCAGCATACCAGCAAAGGC<br>GAAAAAATTGCGATGCTGATGGCGGCGCCGG<br>GCCAGGTGATTCGCGCGAAAACCACCCGCGTG<br>ACCCCGCGCCCGGCGGGCCTGTGGCAGCGCCC<br>GGTGTAA |  |

Example 1. Production of *E. coli* Based on STAPL System and Assessment of Plasmid Number Maintenance in STAPL System In order to construct an auxotrophic complementation (auxotrophic complementation) system based on STAPL, an experiment where an essential gene in the chromosome (chromosome) was removed and the essential gene was expressed in the plasmid was conducted. IF-1 protein is directly related to the viability of the cell, thus minimizing the cross-feeding effect (cross-feeding effect). Thus, infA for encoding the translation initiation factor-1 (IF-1) was selected as the regulatory gene. Then, a plasmid containing an expression cassette expressing the regulatory gene was designed. The plasmid for introducing infA into the strain employed pCDFduet known to have an intermediate copy (40 copies per cell) and CloDF13 was employed as the replication origin (replicon).

First, the infA expressing cassette was constructed to include the intermediate intensity constitutive promoter (J23116) and the low intensity 5'-UTR exhibiting 1115.3 value computationally designed by the UTR designer, and a synthetic terminator (BBa_B1002). Thus, the expression cassette was designed so that the infA expression level was low because the plasmid-based expression system exists in multiple copy numbers, and thus cloning the infA in the same amount as the expression amount thereof on the chromosome may put the stress on the cell and interfere with the growth thereof. In order to indirectly observe the plasmid copy number (PCN), eGFP was expressed as a reporter protein under the strong constitutive promoter (J23100) and 5'-UTR in the same plasmid.

To this end, the infA gene was amplified by using a chromosome of the W3110 strain of *Escherichia coli* as a template and using the O-infA-Flv1/O-infA-F2/O-infA-B primer set of Table 3. The amplified infA gene was inserted into the plasmid via cloning using Bsu36I restriction enzyme sequence. Subsequently, eGFP was amplified using the O-eGFP-F1/O-eGFP-F2/O-eGFP-B primer set. The amplified eGFP was inserted into the plasmid via cloning using SacI restriction enzyme sequence. In this way, pSTAPL_eGFPv1 plasmid was finally constructed.

The completed plasmid was inserted into the W3110 strain of *Escherichia coli*. Then, to remove the infA gene from the chromosome of the strain for the auxotrophic complementation system, the previously known Lambda-Red recombination system was used and pKD46 plasmid was used. A DNA fragment for the infA removal employed FRT-Kan$^R$-FRT as a template. Amplification using a primer set of D-infA-F/D-infA-B was conducted. Thus, the recombinant *E. coli* strain STG1 in which infA was removed was produced. FIG. 1 shows the recombinant plasmid and strain as produced by the above process.

To evaluate the long term stability of the plasmid in the recombinant *E. coli* to which the STAPL was applied, the recombinant *E. coli* was subjected to the cell culture together with *E. coli*(STG0) with a conventional antibiotic-dependent plasmid maintenance system.

All recombinant strains, including recombinant *E. coli* pSTAPL_eGFPv1, were seeded in 3 ml of modified glucose M9 medium as a medium condition for plasmid stability testing (In this connection, the medium contained 100 mM phosphate buffer, 0.5 g/L MgSO$_4$·7H$_2$O, 2 g/L NH$_4$Cl, 2 g/L NaCl and 1 g/L casamino acid, and employed only 20 g/L glucose as the carbon source). Thereafter, the recombinant strains were incubated at 37° ° C. at 250 rpm, and a series of subculture was performed thereto every 5 generations for 40 generations. An initial cell concentration was diluted to an OD$_{600}$ concentration of 0.05 in order to be identical to that of the cells prepared previously via culture in the same medium. An antibiotic for plasmid maintenance employed 50 µg/ml of streptomycin.

Cell growth during the culturing was quantitated by measuring absorbance at 600 nM wavelength using UV-1700 spectrophotometer. Cell fluorescence was measured using a VICTOR 1420 multilabel plate reader and a 486 nm wavelength filter and a 535 nm emission filter. The cells were washed with phosphate-buffered saline (phosphate-buffered saline, PBS), and then fluorescence per cell was measured using S3e cell sorter. FIG. 2 shows the plasmid segregational instability phenomenon with or without antibiotics, and the process in which the plasmid was stably maintained in the STAPL-based strain. Plasmid maintenance ratios for an STG1 E. coli strain containing the recombinant vector according to the present invention and STG0 E. coli strain without the STAPL application thereto subjected to culturing for 40 generations (FIG. 3A) and a fluorescence profile versus the number of cells for the STG1 E. coli strain containing the recombinant vector according to the present invention and STG0 E. coli strain without the STAPL application thereto subjected to culturing for each of 0, 10, 20, and 40 generations (FIG. 3B) were shown in FIG. 3.

As shown in FIG. 2 and FIG. 3A and FIG. 3B, in the STG0 strain without antibiotics, cells without plasmids occurred in a ratio of 56.2% in the 10th generation, and fluorescence ratio was 13.7% at the 40th generation. Thus, it was confirmed that the ratio of maintaining the plasmid in the strain was drastically decreased in the STG0 strain without antibiotics. Further, in the STG0 strain with antibiotic added thereto, no plasmid-free cells occurred, but the cell group with less plasmid occurred in a ratio of 12.3%. After incubation, the fluorescence ratio was found to be 65% at the 40th generation compared with the 0th generation. To the contrary, in the STG1 strain to which the STAPL was applied, the fluorescence ratio was maintained at a ratio close to 100% for 40 generations without addition of antibiotics thereto. The fluorescence ratio was 97.2% in the 40th generation compared with 0th generation. The cell populations having the plasmids were uniformed in the strain. This indicated that the intrinsic mutations were few. Comprehensively, it was confirmed that, in comparison between the conventional antibiotic-dependent plasmid maintenance systems and the present STAPL system, the plasmid could be stably maintained for a long time using the recombinant E. coli which the STAPL system was applied to.

Example 2. Application of STAPL System to Multiple Plasmid System

To construct an auxotrophic complementation system based on the STAPL for two plasmids, two essential genes on chromosome were removed and the essential genes were expressed in each of the plasmids. The infA for encoding the translation initiation factor-1 (IF-1) directly related to cell viability and thus minimizing the cross-feeding effect and efp for encoding a protein elongation factor (EF-P) were selected as a regulatory gene in the expression cassette. Thus, the present STAPL system was constructed. The plasmid for introducing efp into the strain which the STAPL system using infA was applied to employed pETduet, which is known to have an intermediate copy level (40 copies per cell). The replication origin (replicon) employed CloE1.

The efp expression cassette contained in the plasmid to introduce the efp was constructed to include an intermediate intensity constitutive promoter (J23116), a 5'-UTR of low intensity of 1169.4 as designed by the UTR designer, and a synthetic terminator (BBa_B1002). In this connection, cloning the efp in the same amount in the plasmid as the expression amount on the chromosome may put the stress on the cell and interfere with growth of the cell. For this reason, the expression cassette was designed so that the efp expression level was low. To observe the PCN indirectly, mCherry was expressed as a reporter protein under the strong constitutive promoter (J23100) and 5'-UTR in the same plasmid.

A control plasmid with mCherry as a template was amplified using the O-mCherry-F1/O-mCherry-F2/O-mCherry-B primer set of Table 2, and then was inserted into pET plasmid via cloning using SacI restriction enzyme sequence. Thus, pET-mCherry plasmid was constructed. To apply the pET plasmid to the STAPL system, the efp gene was amplified by using the chromosome of the W3110 strain of Escherichia coli as a template and using the O-efp-F1/O-efp-F2/O-efp-B primer set in Table 3. Then, cloning of the efp gene was performed using the XhoI restriction enzyme sequence such that the efp gene was inserted into the pET-mCherry plasmid as prepared above. The, the thus produced plasmid was inserted into the STG1 strain having the infA expression cassette introduced thereto including J23116 as a constitutive promoter having an intensity similar to that of the promoter in the expression cassette of the STG1 strain of Example 1 in which the infA gene was used as a regulatory gene and to which the STAPL system was applied.

Thereafter, prior to removal of efp on the chromosome of the STG1 strain for auxotrophic complementation system, recombination was carried out using pCP20 plasmid to remove the kanamycin resistance gene on the chromosome. The previously known Lambda-Red recombination system and the pKD46 plasmid were used to remove the efp on the chromosome. The recombinant Escherichia coli STGC1 in which the efp on the chromosome was removed for auxotrophic complementation system was produced by amplifying the DNA fragment for removing efp on the chromosome using pFRT2161 as a template and using D-efp-F/D-efp-B primer set in Table 3. In order to evaluate the long-term stability of plasmid in the recombinant E. coli to which the thus produced multiple plasmid STAPL was applied, the recombinant E. coli was subjected to the cell culture together with E. coli(STGC0) with a conventional antibiotic-dependent plasmid maintenance system.

The STGC0 and STGC1 strains were seeded in 3 ml of modified glucose M9 medium as a medium condition for plasmid stability testing (In this connection, the medium contained 100 mM phosphate buffer, 0.5 g/L $MgSO_4 \cdot 7H_2O$, 2 g/L $NH_4Cl$, 2 g/L NaCl and 1 g/L casamino acid, and employed only 4 g/L glucose as the carbon source). Thereafter, the recombinant strains were incubated at 37° C. at 250 rpm, and a series of subculture was performed thereto every 5 generations for 40 generations. An initial cell concentration was diluted to an $OD_{600}$ concentration of 0.05 in order to be identical to that of the cells prepared previously via culture in the same medium. For a conventional antibiotic-dependent plasmid maintenance system (STGC0) used as a positive control, streptomycin and ampicillin of 50 μg/ml were added to the medium as an antibiotic for plasmid maintenance. In this state, the culturing was conducted.

Cell growth during the culturing was quantitated by measuring absorbance at 600 nM wavelength using UV-1700 spectrophotometer. eGFP fluorescence was measured using a VICTOR 1420 multilabel plate reader and a 486 nm wavelength filter and a 535 nm emission filter. The mCherry fluorescence was measured using a Hidex Sense microplate reader, a 575 nm wavelength filter and a 610 nm emission filter, and the measured fluorescence results are shown in FIG. 4A and FIG. 4B.

As shown in FIG. 4A, in the STGC0 strain without antibiotics, the number of the pCDF plasmids was found to be reduced at a strain of a 40-th generation when compared to that of the 0th generation, and, thus, to have a fluorescence ratio of 6.6% at the strain of a 40-th generation. In the STGC0 strain with antibiotics, the pCDF plasmid showed a fluorescence ratio of 62.4% at the strain of a 40-th generation. Thus, the fluorescence ratio in the STGC0 strain was higher than that of STGC0 strain. However, it was confirmed that the number of plasmids in the STGC0 strain decreased during repeated subcultures. To the contrary, in the STGC1 strain in which the STAPL was applied to multiple plasmids, the high fluorescence ratio was maintained for 40 generations even without the addition of antibiotics thereto. The number of the plasmids gradually increased during repeated subcultures, such that the fluorescence ratio was increased to 169.6% in the strain in 40th generation. As shown in FIG. 4B, for the pET plasmid, the STGC0 strain was also found to have a low number of plasmids regardless of whether antibiotics were added or not thereto. Specifically, the strains without antibiotics showed a fluorescence ratio of 11.6% after 40th generation. For the strain having antibiotics added thereto, the fluorescence ratio was 78.5% after 40th generation. The STGC1 strain with the STAPL system applied thereto was found to maintain the plasmids stably for 40 generations without the addition of antibiotics thereto. In this STGC1 strain, the fluorescence ratio increased as the generation increased. In the strain of the 40-th generation, the fluorescence ratio was 247%, thus confirming that the number of plasmids was very stable. Comprehensively, when the antibiotic-dependent plasmid maintenance systems and STAPL systems were compared with each other, it was confirmed that, in the STAPL system, the plasmid could be maintained for a long time even when the efp gene as well as infA gene were used as the regulatory gene. We also confirmed that the number of plasmids in the recombinant strain can be maintained for a long time by applying the STAPL system to multiple plasmids.

Example 3. Application of STAPL System to High Copy Number Plasmid

It is common that, in the high copy number plasmid (high copy plasmid), the copy number decreases sharply because of the large probability variation of the plasmid. However, experiments were conducted to determine whether the PCN is maintained stably in the high copy number plasmid when applying the STAPL system according to the present invention to the high copy number plasmid. To introduce the STAPL system into the high copy plasmid system, essential genes were expressed in the plasmid and the same essential genes on the chromosome were removed. The infA gene for encoding the translation initiation factor-1 (IF-1), which is directly associated with cell viability and can minimize the cross-feeding effect, was selected as the regulatory gene of the expression cassette. Thus, the STAPL system was constructed. The plasmid for introducing the infA gene employed pUC19, which is known to have a high copy number (500 copies per cell). The replication origin (replicon) employed pMB1.

The infA expression cassette included in the plasmid for introducing infA was constructed to include a low intensity constitutive promoter (J23112), 5'-UTR of a low intensity of 263.75 designed by the UTR designer, and a synthetic terminator (BBa_B1002). Cloning this gene in the same amount as the expression amount on the chromosome may put stress on the cell and interfere with growth of the cell. Thus, the expression cassette was designed to have a low infA expression level. To observe PCN indirectly, eGFP was expressed as a reporter protein under the strong constitutive promoter (J23118) and 5'-UTR in the same plasmid.

The control plasmid having pUC19 as a template was amplified using a pUC19-F/O-pUC19-B primer set of Table 3. eGFP having eGFP as a template was amplified using O-eGFP-F1v2/O-eGFP-F2v2/O-eGFP-Bv2 primer set in Table 3. Then, the amplified eGFP was inserted into the pUC19 plasmid via cloning using Bsu36I and XhoI restriction enzyme sequences. Thus, the pUC19-eGFP plasmid was constructed. In order to apply the pUC19 plasmid to the STAPL system, infA gene was amplified using the chromosome of W3110 strain of Escherichia coli as a template and using the O-infA-Flv2/O-infA-F2v2/O-infA-B1v2/O-infA-B2v2 primer set of Table 3. Subsequently, cloning of the gene was performed using SacI and AatII restriction enzyme sequences and then was inserted into the previously prepared pUC19-eGFP plasmid, thereby to construct pSTAPL_eGFPv7.

Subsequently, in order to remove the infA on the chromosome of the STG6 strain for the auxotrophic complementation system, the pKD46 plasmid was used and the previously known Lambda-Red recombination system was used. The recombinant Escherichia coli STG7 in which the infA on the chromosome was removed for auxotrophic complementation system was produced by amplifying the DNA fragment for removing infA on the chromosome using pFRT72 as a template and using D-infA-F/D-infA-B primer set in Table 3. In order to evaluate the long-term stability of plasmid in the recombinant E. coli to which the thus produced multiple plasmid STAPL was applied, the recombinant E. coli was subjected to the cell culture together with E. coli(STG6) with a conventional antibiotic-dependent plasmid maintenance system.

Then, the STG6 and STG7 strains were seeded in 3 ml of modified glucose M9 medium as a medium condition for plasmid stability testing (In this connection, the medium contained 100 mM phosphate buffer, 0.5 g/L MgSO$_4$·7H$_2$O, 2 g/L NH$_4$Cl, 2 g/L NaCl and 1 g/L casamino acid, and employed only 4 g/L glucose as the carbon source). Thereafter, the recombinant strains were incubated at 37° C. at 250 rpm, and a series of subculture was performed thereto every 5 generations for 40 generations. An initial cell concentration was diluted to an OD$_{600}$ concentration of 0.05 in order to be identical to that of the cells prepared previously via culture in the same medium. For a conventional antibiotic-dependent plasmid maintenance system (STG6) used as a positive control, ampicillin of 50 μg/ml was added to the medium as an antibiotic for plasmid maintenance. In this state, the culturing was conducted.

Cell growth during the culturing was quantitated by measuring absorbance at 600 nM wavelength using UV-1700 spectrophotometer. eGFP fluorescence was measured using a VICTOR 1420 multilabel plate reader and a 486 nm wavelength filter and a 535 nm emission filter. The measured fluorescence results are shown in FIG. 5.

As shown in FIG. 5, in the STG6 strain without antibiotics, the number of the pUC19 plasmids showed a decrease in the strain of the 40th generation compared to that of the 0th generation. Thus, the STG6 strain showed a fluorescence ratio of 37.7%. For the pUC19 plasmid in the antibiotic-added STG6 strain, the fluorescence ratio value was 54.6% as detected in the strain of the 40-th generation, which was higher than that of the STG6 strain added with antibiotics. However, it was confirmed that the number of plasmids decreased during repeated subcultures in the antibiotic-added STG6 strain. To the contrary, in the STG7 strain in which the STAPL was applied to the plasmid with high copy numbers, the plasmid maintained the high fluorescence during 40 generations even without the addition of antibiotics thereto. Thus, the plasmid number was maintained stably during repeated subcultures, such that the fluorescence ratio was increased to 79.5% in the strain at the 40th generation. Comprehensively, when the antibiotic-dependent plasmid maintenance systems and STAPL systems were compared with each other, it was confirmed that the plasmid can be stably maintained for a long time even for a plasmid having a high copy number in the STAPL system.

Example 4. PCN Control in STAPL

The expression amount of infA, which is essential for cell survival, has been determined. Thus, experiments were conducted to determine whether PCN could be regulated by controlling the level of transcription using a mechanism of regulating the amount of infA expression in the cells. Additional STG2-5 strains with four different infA expression amounts based on the infA expression amount of *E. coli* STG1 used in Example 1 were produced.

InfA cassettes with promoters of different intensities were amplified with O-infA-Flv2-5/O-infA-B primer set. Then, the amplified infA cassettes were inserted into the plasmid via cloning using Bsu36I restriction enzyme sequence. Thus, the pSTAPL_eGFPv2-5 plasmid was finally constructed. The completed plasmid was inserted into the W3110 strain of *Escherichia coli*, and then the infA on the chromosome was removed for the auxotrophic complementation system. To remove the infA gene, the conventionally known Lambda-Red recombination system was used and pKD46 plasmid was used. The DNA fragment for the infA removal was amplified using the FRT-Kan$^R$-FRT template and the D-infA-F/D-infA-B primer set. In addition to the STG1 produced in Example 1, additional recombinant *Escherichia coli* STG2-5 strains in which infA on the chromosome was removed were produced.

The amount of an actually transferred infA transcript was measured by performing RT-qPCR with the StepOnePlus real-time PCR system while the promoter intensities in the actual system varied. In order to amplify the infA transcript, Q-infA-F/Q-infA-B primer set was used. hcaT and cysG as chromosomal housekeeping genes were defined as a reference. Q-hcaT-F/Q-hcaT-B and Q-cysG-F/Q-cysG-B primer sets were used to amplify the hcaT and cysG transcripts. The relative amount of the infA transcript was quantified using the CT comparison method and the relative intensities were shown in Table 2. The predicted intensities of the promoters as used and the actual expression levels were slightly different from each other, but substantial trends are the same therebetween.

The PCN was defined as the number of plasmids per chromosome. The PCN was measured by using the StepOnePlus Real-time PCR system and by performing quantitative polymerase chain reaction (qPCR). Q-pCDF-F/Q-pCDF-B and Q-polA-F/Q-polA-B primer sets were used to amplify the plasmid and specific portions of the chromosome. Finally, STAPL strains with infAs inserted thereto with 5 different expression amounts were cultured in the same medium as that used in Example 1 of 20 ml. The mechanism of PCN regulation via the mechanism of expression amount adjustment of infA is shown in FIG. 6. Specific fluorescence in the antibiotic-free medium of the STG1-5 strains is shown in FIG. 7A. The actual PCN and relative promoter intensities of infA are shown in FIG. 7B. A strain-specific growth rate is shown in FIG. 7C. FIG. 8 shows a fluorescence profile versus the number of cells for STG2-5 strains according to the present invention subjected to culturing for each of 0, 10, 20, and 40 generations.

As shown in FIG. 7A, it was confirmed that the relative value of the specific fluorescence decreases based on the level of transcription of infA. Further, FIG. 7B confirmed that the PCN value of the cells varies based on the transcription level of infA. From the same experimental results, we confirmed that PCN can be successfully regulated by controlling the amount of infA expression via the regulation of the transcription level of the essential gene based on the control of the promoter intensity. This is because of the following reason: as shown in FIG. 6, when the infA expression amount or level is low, the cells require more infA for survival, so that cells having many plasmids are selected and survive, whereas when the infA expression amount or level is low, it is not necessary to maintain a large number of plasmids, which impose metabolism burden to the cells, and, thus, the cells with fewer plasmids are dominant. That is, as shown in FIG. 7A and FIG. 7B, when adjusting the infA expression amount or level, the PCN can be controlled, and, thus, the PCN value can be quantitatively adjusted up to 5.6 times. The PCN values as thus controlled are summarized in Table 4.

As shown in FIG. 7C, the specific growth rates of the strains STG1-5 are 0.47 h$^{-1}$ and thus are similar. We confirmed from this fact that the STAPL system according to the present invention does not cause metabolic stress on the cells. Further, as shown in FIG. 8, in the STG2 to 5 strains, fluorescence per each cell was stably maintained even when the number of generations was increased as continuous subculture proceeds as in the STG1 strain in Example 1 above.

Thus, it was confirmed that the STAPL system according to the present invention is able to precisely control the amount of expression of infA, such that PCN can be quantitatively regulated up to 5.6 times without imposing additional metabolic stress on the cells expressing the STAPL system.

Example 5. Production of Target Product Via STAPL 5.1 Production of Itaconic Acid Using STAPL System When using the STAPL system according to the present invention, the strain applied to the system can maintain the plasmid stably for a long time while minimizing the intercellular variation, as compared with the conventional antibiotic-dependent plasmid maintenance system. Further, the present STAPL system can finely tune the PCN by adjusting the infA expression amount or level. Therefore, we have conducted an experiment to check that the itaconic acid (itaconic acid) which is a target product, can be produced efficiently by using the present STAPL system. In order to produce the itaconic acid as the target product from *E. coli*, cad foreign gene derived from *Aspergillus terreus* was purchased in a codon-optimized form from Thermo Fisher company. To maximize the amount of the gene expression, we used an expression cassette including the tac promoter and synthetic 5' UTR. The synthetic 5' UTR was designed to maximize the expression amount of the gene. We used the synthetic 5' UTR designed to have more than 1 million predicted expression amount using the UTR Designer. To construct the pCDF-CAD plasmid, a pCDFDuet plasmid having an intermediate copy number was used as a template and was amplified using the O-pCDF-F/O-pCDF-B primer set shown in Table 3. The cad gene was sequentially amplified using O-cad-F1/O-cad-B1 and O-cad-F2/O-cad-B2 primer sets. The amplified gene was inserted into the plasmid via cloning using BsaI restriction enzyme sequence. The pCDF-CAD plasmid was finally constructed. To construct pSTAPL_CAD_v1-5 with the STAPL system applied to the plasmid, the infA gene was amplified by using the chromosome of W3110 strain of *Escherichia coli* as a template and using the O-infA-Flv1-5/O-infA-F2/O-infA-B primer set of Table 3. Then, the amplified gene was inserted into the plasmid via cloning using Bsu36I restriction enzyme sequence. The completed plasmid was inserted into the W3110 strain of *Escherichia coli*. Next, in order to remove the infA on the chromosome in the strain for the auxotrophic complementation system, the previously known Lambda-Red recombination system was used and pKD46 plasmid was used. The DNA fragment for the infA removal was amplified using FRT-Kan$^R$-FRT as a template and by using D-infA-F/D-infA-B primer set. Thus, the infA-removed recombinant *E. coli* STI1-5 strains were produced.

To analyze the production amount of itaconic acid produced from the recombinant *E. coli*, the above recombinant *E. coli* was cultured together with a negative control and positive control (STI0). The recombinant *E. coli* strains STI 0-5 were input in 25 ml of modified glucose M9 (In this connection, the medium contained 100 mM phosphate buffer, 0.5 g/L MgSO$_4$·7H$_2$O, 2 g/L NH$_4$Cl, 2 g/L NaCl, 2 g/L yeast extract, and 10 mL/L ATCC trace mineral solution, and employed only 20 g/L glucose as the carbon source). Thereafter, the recombinant strains were incubated at 30° C. at 200 rpm for 48 hours. An initial cell concentration was diluted to an OD$_{600}$ concentration of 0.05 in order to be identical to that of the cells prepared previously via culture in the same medium. Only for a conventional antibiotic-dependent plasmid maintenance system (STI0) used as a positive control, streptomycin of 50 µg/ml was added to the medium as an antibiotic for plasmid maintenance. In this state, the culturing was conducted. After incubation, itaconic acid and other organics in the medium were measured using the Aminex HPX-87H column and 0.6 ml of 5 mM H$_2$SO$_4$ per minute in the mobile phase. Shodex RI-101 instrument was used for detection. The STAPL system and corresponding plasmids for the production of itaconic acid are shown in FIG. 9. The results of the production of itaconic acid using STI0-5 strains after 30 hours are shown in FIG. 10A, and the corresponding PCN is shown in 10B.

As shown in FIG. 10A, in the STI0 strain without antibiotics, from the result after 30 hours, the production amount of 0.28 g/L of itaconic acid as negligible compared with other strains used was confirmed. The production amount of 0.42 g/L as approximately twice larger as the production amount of 0.28 g/L in the STI0 strain was observed for the STI0 strain containing antibiotics. To the contrary, the STAPL-based production systems that do not contain the antibiotics have the lowest infA expression level. Thus, in the STI1 strain with the highest PCN, the production amount of 0.69 g/L of the itaconic acid, which is 170% greater than that of the STI0 strain containing the antibiotics, was identified. Other strains with the STAPL-based production system applied thereto showed a value of about 0.6 g/L. These results indicate that the strain having a high PCN is advantageous for production at the early stage of culturing because the cell growth is fast at the early stage of culturing, but the strain having a low PCN is advantageous for production since the cell is not grown after the early stage of culturing. Further, as shown in FIG. 10B, after 30 hours of the culturing, the PCN was found to decrease with increasing infA expression level. More specifically, the lowest value of a copy number of 663 was found in STI4 strain. In the STI1 strain, the maximum value of the PCN was found to be 3390 copy number. The detailed values are shown as the corresponding PCN values in Table 4. Comprehensively, it was confirmed that the STAPL could successfully maintain the plasmid number in the itaconic acid production system. It was further confirmed that the STAPL may be applied to find the optimal expression level of the target gene to maximize the production of the itaconic acid.

Example 5.2 Production of Lycopene Using STAPL System

An experiment was conducted to evaluate whether the present STAPL system could be used to efficiently produce the target product lycopene (Lycopene), based on the analysis of the STAPL-applied strains in the Examples 1 to 3. The production aspect of lycopene by using the present STAPL system was compared and analyzed while the lycopene was defined as the target product. For production of lycopene, ispA and idi derived from *Escherichia coli* and crtEBI derived from *Pantoea agglomerans* were purchased in a codon-optimized form Thermo Fisher company. To construct pSTAPL_LYCv1-5 with the STAPL applied thereto using the pCDF_idi_ispA_crtEBI plasmid shown in Table 1, infA gene was amplified using the chromosome of W3110 strain of *Escherichia coli* as a template and by using the O-infA-Flv1-5/O-infA-F2/O-infA-B primer set of Table 3. Then, the amplified gene was inserted into the plasmid via cloning using Bsu36I restriction enzyme sequence. The completed plasmid was inserted into the W3110 strain of *Escherichia coli*. Next, in order to remove the infA on the chromosome in the strain for the auxotrophic complementation system, the previously known Lambda-Red recombination system was used and pKD46 plasmid was used. The DNA fragment for the infA removal was amplified using FRT-Kan$^R$-FRT as a template and by using D-infA-F/D-infA-B primer set. Thus, the infA-removed recombinant *E. coli* STI1-5 stains were produced.

To analyze the production amount of lycopene produced from the recombinant *E. coli*, the above recombinant *E. coli* was cultured together with a negative control and positive control (STL0). The recombinant *E. coli* strains STL0-5 were seeded in 20 ml of modified glucose 2× M9 medium (In this connection, the medium contained 200 mM phosphate buffer, 1 g/L MgSO$_4$·7H$_2$O, 4 g/L NH$_4$Cl, and 4 g/L NaCl, and employed only 4 g/L glucose as the carbon source). Thereafter, the recombinant strains were incubated at 37° ° C. at 250 rpm for 24 hours. An initial cell concentration was diluted to an OD$_{600}$ concentration of 0.05 in order to be identical to that of the cells prepared previously via culture in the same medium. Only for a conventional antibiotic-dependent plasmid maintenance system (STL0) used as a positive control, streptomycin of 50 µg/ml was added to the medium as an antibiotic for plasmid maintenance. In this state, the culturing was conducted. After incubation, the amount of lycopene production was measured using a known modified colorimetric assay (colorimetric assay) and quantified via a 475 nm absorbance measurement using a VICTOR 1420 Multilabel Plate Reader. The STAPL system for the lycopene production and the corresponding plasmids are shown in FIG. 11. FIG. 12A shows the specific production aspect of the lycopene after 24 hours of the STL0-5 strains culture. PCN at OD of 0.8 is shown in FIG. 12B.

As shown in FIG. 12A, the specific production trend of lycopene was inversely related to the promoter intensity of infA, thus confirming that they are closely related. As the infA expression level is higher, the PCN is kept low, so the gene level of the lycopene-producing genes was relatively decreased and the carbon flux for the lycopene synthesis was reduced. Consequently, the specific production level of the lycopene decreased. In particular, it was confirmed that the STL1 strain, which has the lowest infA expression level and thus has the highest PCN, exhibited a high lycopene production amount of 27.1 mg/g DCW, which is 200% higher than that of the STL0 strain containing antibiotics. As shown in FIG. 12B, after 30 hours of the culturing, the PCN was found to decrease with increasing infA expression level. More specifically, the lowest value of 38 copy number was found in STI4, and the highest value of 684 copy number was found in STI1. The detailed values are shown as corresponding PCN values in Table 4. Comprehensively, we confirmed that the STAPL can successfully maintain the plasmid in the lycopene production system. Further, we confirmed that the present STAPL can be applied to find the optimal expression level of the target gene to maximize the production of the lycopene.

According to the present embodiment, when the STAPL system using the infA and having *Escherichia coli* as a host cell is applied, the PCN can be finely and quantitatively regulated according to the expression level of the infA. Thus, the present system has been applied to solve the conventional problem that the expensive antibiotics must be added to the medium and to effectively control the PCN.

Although the present invention has been described with reference to the preferred embodiments, the skilled person to the art may make various modifications and variations without departing from the spirit and scope of the invention. Further, the appended claims include such modifications or variations that fall within the spirit of the present invention.

The invention claimed is:

1. A gene expression cassette containing a synthetic 5' UTR (untranslated region), a promoter, and a regulatory gene, wherein the synthetic 5' UTR includes one 5' UTR selected from a group consisting of SEQ ID NOs: 54, 55, 56 and 59.

2. The gene expression cassette of claim 1, wherein the regulatory gene includes at least one selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, secD, secF, ribD, ribE, nusB, thiL, dxs, ispA, ffs, dnaX, adk, hemH, lpxH, cysS, folD, argU mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, me, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, vejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, vqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, yidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, orn, yjeE, rpsR, ppa, valS, yjgP, yjgQ, dnaC and dnaT.

3. The gene expression cassette of claim 1, wherein the promoter includes one promoter selected from a group consisting of SEQ ID NOS: 1 to 5.

4. The gene expression cassette of claim 1, wherein the synthetic 5' UTR is configured to down-regulate a gene.

5. The gene expression cassette of claim 1, wherein the gene expression cassette further includes a target gene.

6. The gene expression cassette of claim 5, wherein the target gene includes an itaconic acid or lycopene-producing gene.

7. The gene expression cassette of claim 1, wherein the gene expression cassette further includes a terminator.

8. The gene expression cassette of claim 7, wherein the terminator consists of SEQ ID NO: 53.

9. A recombinant vector comprising a replication origin and the gene expression cassette of claim 1.

10. The recombinant vector of claim 9, wherein the recombinant vector is a plasmid.

11. The recombinant vector of claim 10, wherein the plasmid includes the replication origin to allow the plasmid to have 1 to 600 copy numbers per cell.

12. The recombinant vector of claim 9, wherein the recombinant vector includes CloDF-13 or PMB1 as the replication origin and includes infA as the regulatory gene.

13. The recombinant vector of claim 9, wherein the recombinant vector includes CloE1 as the replication origin and includes efp as the regulatory gene.

14. A recombinant microorganism having alleviated segregational instability (segregational instability), wherein the recombinant microorganism has the recombinant vector of claim 9 introduced thereto.

15. A recombinant microorganism having alleviated segregational instability (segregational instability), wherein the recombinant microorganism has one or more recombinant vectors introduced thereto selected from a group consisting of the recombinant vector of claim 12 and the recombinant vector of claim 13.

16. The recombinant microorganism having alleviated segregational instability (segregational instability) of claim 14, wherein the recombinant microorganism stably maintains the number of the recombinant vectors therein.

17. The recombinant microorganism having alleviated segregational instability (segregational instability) of claim 14, wherein one or more regulatory genes selected from a group consisting of iiribF, ileS, IspA, ispH, dapB, folA, imp, ftsL, ftsI, murE, murF, mraY, murD, ftsW, murG, murC, ftsQ, ftsA, ftsZ, lpxC, secM, secA, coaE, can, folk, hemL, yadR, dapD, map, rpsB, tsf, pyrH, frr, dxr, ispU, cdsA, yaeL, yaeT, lpxD, fabZ, lpxA, lpxB, dnaE, accA, tilS, proS, hemB, secD, secF, ribD, ribE, nusB, thiL, dxs, ispA, ffs, dnaX, adk, hemH, lpxH, cysS, folD, argU, mrdB, mrdA, nadD, holA, rlpB, leuS, lnt, leuW, glnS, fldA, infA, ftsK, lolA, serS, rpsA, msbA, lpxK, kdsB, mukF, mukE, mukB, asnS, fabA, serT, mviN, me, yceQ, fabD, fabG, acpP, tmk, holB, lolC, lolD, lolE, pth, prsA, ispE, lolB, hemA, prfA, prmC, kdsA, topA, ribA, fabI, tyrS, ribC, pheT, pheS, rplT, infC, thrS, nadE, gapA, yeaZ, aspS, argS, leuZ, cysT, pgsA, metG, folE, vejM, gyrA, nrdA, nrdB, folC, accD, fabB, gltX, ligA, zipA, dapE, dapA, hda, der, hisS, ispG, suhB, acpS, era, lepB, pssA, yfiO, rplS, trmD, rpsP, ffh, grpE, yfjB, serV, csrA, alaS, ispF, ispD, ftsB, eno, pyrG, lgt, prfB, fbaA, pgk, metK, yqgF, plsC, parC, parE, ribB, cca, folB, ygjD, dnaG, rpoD, infB, nusA, leuU, glmM, ftsH, obgE, rpmA, rplU, ispB, murA, kdsC, yrbK, yhbN, yhbG, rpsI, rplM, degS, mreD, mreC, mreB, accB, accC, rpoC, rpoB, rplL, rplJ, nusG, secE, glyT, thrU, coaA, birA, murB, murI, priA, ftsN, yihA, polA, hemG, hemC, hemD, proM, hisR, argX, rho, trpT, glmU, glmS, yidC, mpA, rpmH, dnaA, dnaN, gyrB, spoT, gmk, dut, dfp, rpmB, coaD, kdtA, gpsA, glyQ, glyS, ftsY, ftsE, ftsX, rpoH, asd, yrfF, trpS, rpsL, rpsG, fusA, rpsJ, rplC, rplD, rplW, rplB, rpsS, rplV, rpsC, rplP, rpmC, rpsQ, rplN, rplX, rplE, rpsN, rpsH, rplF, rplR, rpsE, rpmD, rplO, secY, rpsM, rpsK, rpsD, rpoA, rplQ, fmt, def, yrdC, ubiA, plsB, lexA, dnaB, ssb, groS, groL, efp, psd, rsgA, orn, yjeE, rpsR, ppa, valS, yjgP, yjgQ, dnaC and dnaT on chromosomes in the recombinant microorganism are removed.

18. A method for preparing a recombinant microorganism having alleviated segregational instability (segregational instability), the method comprising introducing the recombinant vector of claim 9 thereto.

* * * * *

SEQUENCE LISTING

<160> NUMBER OF SEQ ID NOS: 68

<210> SEQ ID NO 1
<211> LENGTH: 35
<212> TYPE: DNA
<213> ORGANISM: Artificial Sequence
<220> FEATURE:
<223> OTHER INFORMATION: J23112 promoter sequence

<400> SEQUENCE: 1
ctgatagcta gctcagtcct agggattatg ctagc                        35

<210> SEQ ID NO 2
<211> LENGTH: 35
<212> TYPE: DNA
<213> ORGANISM: Artificial Sequence
<220> FEATURE:
<223> OTHER INFORMATION: J23109 promoter sequence

<400> SEQUENCE: 2
tttacagcta gctcagtcct agggactgtg ctagc                        35

<210> SEQ ID NO 3
<211> LENGTH: 35
<212> TYPE: DNA
<213> ORGANISM: Artificial Sequence
<220> FEATURE:
<223> OTHER INFORMATION: J23116 promoter sequence

<400> SEQUENCE: 3
ttgacagcta gctcagtcct agggactatg ctagc                        35

<210> SEQ ID NO 4
<211> LENGTH: 35
<212> TYPE: DNA
<213> ORGANISM: Artificial Sequence
<220> FEATURE:
<223> OTHER INFORMATION: J23118 promoter sequence

<400> SEQUENCE: 4
ttgacggcta gctcagtcct aggtattgtg ctagc                        35

<210> SEQ ID NO 5
<211> LENGTH: 35
<212> TYPE: DNA
<213> ORGANISM: Artificial Sequence
<220> FEATURE:
<223> OTHER INFORMATION: J23100 promoter sequence

<400> SEQUENCE: 5
ttgacggcta gctcagtcct aggtacagtg ctagc                        35

```
<210> SEQ ID NO 6
<211> LENGTH: 22
<212> TYPE: DNA
<213> ORGANISM: Artificial Sequence
<220> FEATURE:
<223> OTHER INFORMATION: primer sequence of C-infA-F

<400> SEQUENCE: 6
gtggcgagtc catgttcagc cg                                              22

<210> SEQ ID NO 7
<211> LENGTH: 22
<212> TYPE: DNA
<213> ORGANISM: Artificial Sequence
<220> FEATURE:
<223> OTHER INFORMATION: primer sequence of C-infA-B

<400> SEQUENCE: 7
aaacctcatg ggtggcaacg gg                                              22

<210> SEQ ID NO 8
<211> LENGTH: 68
<212> TYPE: DNA
<213> ORGANISM: Artificial Sequence
<220> FEATURE:
<223> OTHER INFORMATION: primer sequence of D-infA-F

<400> SEQUENCE: 8
tgccgaataa tttctgggta ccacgatgct tgttttcacc acaagaatga gcatgaccgg    60
cgcgatgc                                                              68

<210> SEQ ID NO 9
<211> LENGTH: 70
<212> TYPE: DNA
<213> ORGANISM: Artificial Sequence
<220> FEATURE:
<223> OTHER INFORMATION: primer sequence of D-infA-B

<400> SEQUENCE: 9
ctcgttcttt ctcttcgccc atcaggcggt aaaacaatca gcgactacgg gctcagcgga    60
tctcatgcgc                                                            70

<210> SEQ ID NO 10
<211> LENGTH: 50
<212> TYPE: DNA
<213> ORGANISM: Artificial Sequence
<220> FEATURE:
<223> OTHER INFORMATION: primer sequence of O-eGFP-F2

<400> SEQUENCE: 10
gagagttcag agctcttgac ggctagctca gtcctaggta cagtgctagc                50

<210> SEQ ID NO 11
<211> LENGTH: 38
<212> TYPE: DNA
<213> ORGANISM: Artificial Sequence
<220> FEATURE:
<223> OTHER INFORMATION: primer sequence of O-eGFP-B

<400> SEQUENCE: 11
gcatgcggct gagctcgcga aaaacccg ccgaagcg                               38

<210> SEQ ID NO 12
```

<211> LENGTH: 48
<212> TYPE: DNA
<213> ORGANISM: Artificial Sequence
<220> FEATURE:
<223> OTHER INFORMATION: primer sequence of O-infA-F2

<400> SEQUENCE: 12
ctgaaacctc aggtttacag ctagctcagt cctagggact gtgctagc    48

<210> SEQ ID NO 13
<211> LENGTH: 65
<212> TYPE: DNA
<213> ORGANISM: Artificial Sequence
<220> FEATURE:
<223> OTHER INFORMATION: primer sequence of O-infA-B

<400> SEQUENCE: 13
cctgagggcg aaaaaacccc gccgaagcgg ggttttttgc gtcagcgact acggaagaca    60
atgcg    65

<210> SEQ ID NO 14
<211> LENGTH: 70
<212> TYPE: DNA
<213> ORGANISM: Artificial Sequence
<220> FEATURE:
<223> OTHER INFORMATION: primer sequence of O-infA-F1v1

<400> SEQUENCE: 14
ctgaaacctc aggttgacag ctagctcagt cctagggact atgctagcgt agtactggaa    60
atgagcatcc    70

<210> SEQ ID NO 15
<211> LENGTH: 70
<212> TYPE: DNA
<213> ORGANISM: Artificial Sequence
<220> FEATURE:
<223> OTHER INFORMATION: primer sequence of O-infA-F1v2

<400> SEQUENCE: 15
ctgaaacctc aggctgatag ctagctcagt cctaggatt atgctagcgt agtactggaa    60
atgagcatcc    70

<210> SEQ ID NO 16
<211> LENGTH: 70
<212> TYPE: DNA
<213> ORGANISM: Artificial Sequence
<220> FEATURE:
<223> OTHER INFORMATION: primer sequence of O-infA-F1v3

<400> SEQUENCE: 16
ctgaaacctc aggtttacag ctagctcagt cctagggact gtgctagcgt agtactggaa    60
atgagcatcc    70

<210> SEQ ID NO 17
<211> LENGTH: 70
<212> TYPE: DNA
<213> ORGANISM: Artificial Sequence
<220> FEATURE:
<223> OTHER INFORMATION: primer sequence of O-infA-F1v4

<400> SEQUENCE: 17
ctgaaacctc aggttgacgg ctagctcagt cctaggtatt gtgctagcgt agtactggaa    60
atgagcatcc    70

<210> SEQ ID NO 18
<211> LENGTH: 70
<212> TYPE: DNA
<213> ORGANISM: Artificial Sequence
<220> FEATURE:
<223> OTHER INFORMATION: primer sequence of O-infA-F1v5

<400> SEQUENCE: 18
ctgaaacctc aggttgacgg ctagctcagt cctaggtaca gtgctagcgt agtactggaa    60
atgagcatcc                                                          70

<210> SEQ ID NO 19
<211> LENGTH: 68
<212> TYPE: DNA
<213> ORGANISM: Artificial Sequence
<220> FEATURE:
<223> OTHER INFORMATION: primer sequence of O-eGFP-F1

<400> SEQUENCE: 19
ctcagtccta ggtacagtgc tagcatcctg cattaaagga gcatccatta tggctagcaa    60
gggcgagg                                                            68

<210> SEQ ID NO 20
<211> LENGTH: 19
<212> TYPE: DNA
<213> ORGANISM: Artificial Sequence
<220> FEATURE:
<223> OTHER INFORMATION: primer sequence of Q-pCDF-F

<400> SEQUENCE: 20
catgttagtc atgccccgc                                                19

<210> SEQ ID NO 21
<211> LENGTH: 20
<212> TYPE: DNA
<213> ORGANISM: Artificial Sequence
<220> FEATURE:
<223> OTHER INFORMATION: primer sequence of Q-pCDF-B

<400> SEQUENCE: 21
ctcactcatt aggcaccggg                                               20

<210> SEQ ID NO 22
<211> LENGTH: 20
<212> TYPE: DNA
<213> ORGANISM: Artificial Sequence
<220> FEATURE:
<223> OTHER INFORMATION: primer sequence of Q-polA-F

<400> SEQUENCE: 22
gcgagcgatc cagaagatct                                               20

<210> SEQ ID NO 23
<211> LENGTH: 21
<212> TYPE: DNA
<213> ORGANISM: Artificial Sequence
<220> FEATURE:
<223> OTHER INFORMATION: primer sequence of Q-polA-B

<400> SEQUENCE: 23
gggtaaagga tgccacagac a                                             21

<210> SEQ ID NO 24

```
<211> LENGTH: 23
<212> TYPE: DNA
<213> ORGANISM: Artificial Sequence
<220> FEATURE:
<223> OTHER INFORMATION: primer sequence of Q-infA-F

<400> SEQUENCE: 24
ggaaatgagc atccagtatg gcc                                              23

<210> SEQ ID NO 25
<211> LENGTH: 25
<212> TYPE: DNA
<213> ORGANISM: Artificial Sequence
<220> FEATURE:
<223> OTHER INFORMATION: primer sequence of Q-infA-B

<400> SEQUENCE: 25
gtagtttttg cgcattttac cggag                                            25

<210> SEQ ID NO 26
<211> LENGTH: 73
<212> TYPE: DNA
<213> ORGANISM: Artificial Sequence
<220> FEATURE:
<223> OTHER INFORMATION: primer sequence of O-cad-F1

<400> SEQUENCE: 26
ggaattgtga gcggataaca attaaaaaaa acaaaaggag catcacccat gaccaaacag       60
agcgcagata gca                                                         73

<210> SEQ ID NO 27
<211> LENGTH: 77
<212> TYPE: DNA
<213> ORGANISM: Artificial Sequence
<220> FEATURE:
<223> OTHER INFORMATION: primer sequence of O-cad-F2

<400> SEQUENCE: 27
catccaggtc tcgggttgac aattaatcat cggctcgtat aatgtgtgga attgtgagcg       60
gataacaatt aaaaaaa                                                     77

<210> SEQ ID NO 28
<211> LENGTH: 69
<212> TYPE: DNA
<213> ORGANISM: Artificial Sequence
<220> FEATURE:
<223> OTHER INFORMATION: primer sequence of O-cad-B1

<400> SEQUENCE: 28
aaaaaaaaac cccgccgaag cggggttttt ttttggtgcg atttaaacca gcggactttt       60
aaccggaca                                                              69

<210> SEQ ID NO 29
<211> LENGTH: 38
<212> TYPE: DNA
<213> ORGANISM: Artificial Sequence
<220> FEATURE:
<223> OTHER INFORMATION: primer sequence of O-cad-B2

<400> SEQUENCE: 29
catccaggtc tcgccaaaaa aaaccccgc cgaagcgg                               38

<210> SEQ ID NO 30
<211> LENGTH: 41
```

```
<212> TYPE: DNA
<213> ORGANISM: Artificial Sequence
<220> FEATURE:
<223> OTHER INFORMATION: primer sequence of O-pCDF-F

<400> SEQUENCE: 30
catccaggtc tcgttggacc tcaggcattt gagaagcaca c                    41

<210> SEQ ID NO 31
<211> LENGTH: 44
<212> TYPE: DNA
<213> ORGANISM: Artificial Sequence
<220> FEATURE:
<223> OTHER INFORMATION: primer sequence of O-pCDF-B

<400> SEQUENCE: 31
catccaggtc tcctcgaacc aggagtcgca taagggagag cgtc                 44

<210> SEQ ID NO 32
<211> LENGTH: 20
<212> TYPE: DNA
<213> ORGANISM: Artificial Sequence
<220> FEATURE:
<223> OTHER INFORMATION: primer sequence of C-efp-F

<400> SEQUENCE: 32
ggcacacgca gggcaaaaag                                            20

<210> SEQ ID NO 33
<211> LENGTH: 79
<212> TYPE: DNA
<213> ORGANISM: Artificial Sequence
<220> FEATURE:
<223> OTHER INFORMATION: primer sequence of C-efp-B

<400> SEQUENCE: 33
attcgaattc gagctcgcga aaaaccccg ccgaagcggg gttttttgcg tcattatttg   60
tacagctcat ccatgccac                                             79

<210> SEQ ID NO 34
<211> LENGTH: 70
<212> TYPE: DNA
<213> ORGANISM: Artificial Sequence
<220> FEATURE:
<223> OTHER INFORMATION: primer sequence of D-efp-F

<400> SEQUENCE: 34
gagggcctta tggcaacgta ctatagcaac gattttcgtg ctggtcttaa accgcatgac   60
cgcgcgatgc                                                       70

<210> SEQ ID NO 35
<211> LENGTH: 70
<212> TYPE: DNA
<213> ORGANISM: Artificial Sequence
<220> FEATURE:
<223> OTHER INFORMATION: primer sequence of D-efp-B

<400> SEQUENCE: 35
ctctgacctg aataagtgat ggtgcagcct gcaggccgca ccacaaccgc cgcgacgaca   60
ggcacatgcg                                                       70

<210> SEQ ID NO 36
<211> LENGTH: 66
<212> TYPE: DNA
```

```
<213> ORGANISM: Artificial Sequence
<220> FEATURE:
<223> OTHER INFORMATION: primer sequence of O-mCherry-F1

<400> SEQUENCE: 36
caggcgcgcc gagctcttga cggctagctc agtcctaggt acagtgctag cccctggatt     60
aaaagg                                                                66

<210> SEQ ID NO 37
<211> LENGTH: 50
<212> TYPE: DNA
<213> ORGANISM: Artificial Sequence
<220> FEATURE:
<223> OTHER INFORMATION: primer sequence of O-mCherry-F2

<400> SEQUENCE: 37
tgctagcccc tggattaaaa ggagcatctt taatggtttc caagggcgag                 50

<210> SEQ ID NO 38
<211> LENGTH: 79
<212> TYPE: DNA
<213> ORGANISM: Artificial Sequence
<220> FEATURE:
<223> OTHER INFORMATION: primer sequence of O-mCherry-B

<400> SEQUENCE: 38
attcgaattc gagctcgcga aaaaccccg ccgaagcggg gttttttgcg tcattatttg      60
tacagctcat ccatgccac                                                  79

<210> SEQ ID NO 39
<211> LENGTH: 67
<212> TYPE: DNA
<213> ORGANISM: Artificial Sequence
<220> FEATURE:
<223> OTHER INFORMATION: primer sequence of O-efp-F1

<400> SEQUENCE: 39
ctagggacta tgctagctcc tgattctcac ataacccaga aaattatggc aacgtactat     60
agcaacg                                                               67

<210> SEQ ID NO 40
<211> LENGTH: 60
<212> TYPE: DNA
<213> ORGANISM: Artificial Sequence
<220> FEATURE:
<223> OTHER INFORMATION: primer sequence of O-efp-F2

<400> SEQUENCE: 40
cgtcggtacc ctcgagttga cagctagctc agtcctaggg actatgctag ctcctgattc     60

<210> SEQ ID NO 41
<211> LENGTH: 74
<212> TYPE: DNA
<213> ORGANISM: Artificial Sequence
<220> FEATURE:
<223> OTHER INFORMATION: primer sequence of O-efp-B

<400> SEQUENCE: 41
ctttaccaga ctcgaggcga aaaaccccg ccgaagcggg gttttttgcg ttacttcacg      60
cgagagacgt attc                                                       74

<210> SEQ ID NO 42
<211> LENGTH: 76
```

```
<212> TYPE: DNA
<213> ORGANISM: Artificial Sequence
<220> FEATURE:
<223> OTHER INFORMATION: primer sequence of FRT2161_F

<400> SEQUENCE: 42
ccgcatgacc gcgcgatgcg aagttcctat actctctgga aataggaac ttctcaagat      60 cccctcacgc tgccgc                                                    76

<210> SEQ ID NO 43
<211> LENGTH: 78
<212> TYPE: DNA
<213> ORGANISM: Artificial Sequence
<220> FEATURE:
<223> OTHER INFORMATION: primer sequence of FRT2161_B

<400> SEQUENCE: 43
cgcgacgaca ggcacatgcg gaagttccta ttctccagag agtataggaa cttcagagcg    60
cttttgaagc tggggtgg                                                  78

<210> SEQ ID NO 44
<211> LENGTH: 37
<212> TYPE: DNA
<213> ORGANISM: Artificial Sequence
<220> FEATURE:
<223> OTHER INFORMATION: primer sequence of O-pUC19-F

<400> SEQUENCE: 44
tttgcgtgaa actcgagcgc caagcttgca tgcctgc                             37

<210> SEQ ID NO 45
<211> LENGTH: 38
<212> TYPE: DNA
<213> ORGANISM: Artificial Sequence
<220> FEATURE:
<223> OTHER INFORMATION: primer sequence of O-pUC19-B

<400> SEQUENCE: 45
aggagtttac cctgaggggc cagcaaaagg ccaggaac                            38

<210> SEQ ID NO 46
<211> LENGTH: 51
<212> TYPE: DNA
<213> ORGANISM: Artificial Sequence
<220> FEATURE:
<223> OTHER INFORMATION: primer sequence of O-eGFP-F1v2

<400> SEQUENCE: 46
tgctagcagg gtgtgcgaaa ggagcatctt taatggctag caagggcgag g             51

<210> SEQ ID NO 47
<211> LENGTH: 69
<212> TYPE: DNA
<213> ORGANISM: Artificial Sequence
<220> FEATURE:
<223> OTHER INFORMATION: primer sequence of O-eGFP-F2v2

<400> SEQUENCE: 47
tttgctgaaa cctcaggttg acggctagct cagtcctagg tattgtgcta gcagggtgtg    60
cgaaaggag                                                            69

<210> SEQ ID NO 48
<211> LENGTH: 25
<212> TYPE: DNA
```

```
<213> ORGANISM: Artificial Sequence
<220> FEATURE:
<223> OTHER INFORMATION: primer sequence of O-eGFP-Bv2

<400> SEQUENCE: 48
gtagtactgg aaatgagcat ccagt                                           25

<210> SEQ ID NO 49
<211> LENGTH: 67
<212> TYPE: DNA
<213> ORGANISM: Artificial Sequence
<220> FEATURE:
<223> OTHER INFORMATION: primer sequence of O-infA-F1v2

<400> SEQUENCE: 49
gtcctaggga ttatgctagc gtagtactgg atttttgcat ccagtatggc caaagaagac     60
aatattg                                                               67

<210> SEQ ID NO 50
<211> LENGTH: 65
<212> TYPE: DNA
<213> ORGANISM: Artificial Sequence
<220> FEATURE:
<223> OTHER INFORMATION: primer sequence of O-infA-F2v2

<400> SEQUENCE: 50
cccgggtacc cccgggtacc gagctcctga tagctagctc agtcctaggg attatgctag     60
cgtag                                                                 65

<210> SEQ ID NO 51
<211> LENGTH: 33
<212> TYPE: DNA
<213> ORGANISM: Artificial Sequence
<220> FEATURE:
<223> OTHER INFORMATION: primer sequence of O-infA-B1v2

<400> SEQUENCE: 51
tcagtgagac ctcagcgact acggaagaca atg                                  33

<210> SEQ ID NO 52
<211> LENGTH: 72
<212> TYPE: DNA
<213> ORGANISM: Artificial Sequence
<220> FEATURE:
<223> OTHER INFORMATION: primer sequence of O-infA-B2v2

<400> SEQUENCE: 52
agtgccacct gacgtcgcga aaaaccccg ccgaagcggg gttttttgcg tcagtgagac      60
ctcagcgact ac                                                         72

<210> SEQ ID NO 53
<211> LENGTH: 34
<212> TYPE: DNA
<213> ORGANISM: Artificial Sequence
<220> FEATURE:
<223> OTHER INFORMATION: BBa_1002 terminator sequence

<400> SEQUENCE: 53
cgcaaaaaac cccgcttcgg cggggttttt tcgc                                 34

<210> SEQ ID NO 54
<211> LENGTH: 219
<212> TYPE: DNA
<213> ORGANISM: Artificial Sequence
```

<220> FEATURE:
<223> OTHER INFORMATION: infA(STG1-5) 5'-UTR sequence

<400> SEQUENCE: 54

```
atggccaaag aagacaatat tgaaatgcaa ggaaccgttc ttgaaacgtt gcctaatacc      60
atgttccgcg tagagttaga aaacggtcac gtggttactg cacacatctc cggtaaaatg     120
cgcaaaaact acatccgcat cctgacgggc gacaaagtga ctgttgaact gaccccgtac     180
gacctgagca aaggccgcat tgtcttccgt agtcgctga                            219
```

<210> SEQ ID NO 55
<211> LENGTH: 25
<212> TYPE: DNA
<213> ORGANISM: Artificial Sequence
<220> FEATURE:
<223> OTHER INFORMATION: infA(STG7) 5'-UTR sequence

<400> SEQUENCE: 55

```
agggtgtgcg aaaggagcat cttta                                            25
```

<210> SEQ ID NO 56
<211> LENGTH: 28
<212> TYPE: DNA
<213> ORGANISM: Artificial Sequence
<220> FEATURE:
<223> OTHER INFORMATION: efp(STGC1) 5'-UTR sequence

<400> SEQUENCE: 56

```
tcctgattct cacataaccc agaaaatt                                         28
```

<210> SEQ ID NO 57
<211> LENGTH: 25
<212> TYPE: DNA
<213> ORGANISM: Artificial Sequence
<220> FEATURE:
<223> OTHER INFORMATION: eGFP(STG0) 5'-UTR sequence

<400> SEQUENCE: 57

```
atcctgcatt aaaggagcat ccatt                                            25
```

<210> SEQ ID NO 58
<211> LENGTH: 25
<212> TYPE: DNA
<213> ORGANISM: Artificial Sequence
<220> FEATURE:
<223> OTHER INFORMATION: eGFP(STG6) 5'-UTR sequence

<400> SEQUENCE: 58

```
agggtgtgcg aaaggagcat cttta                                            25
```

<210> SEQ ID NO 59
<211> LENGTH: 25
<212> TYPE: DNA
<213> ORGANISM: Artificial Sequence
<220> FEATURE:
<223> OTHER INFORMATION: mCherry(STGC0) 5'-UTR sequence

<400> SEQUENCE: 59

```
ccctggatta aaaggagcat cttta                                            25
```

<210> SEQ ID NO 60
<211> LENGTH: 219
<212> TYPE: DNA
<213> ORGANISM: Unknown
<220> FEATURE:

<223> OTHER INFORMATION: infA sequence originated from Escherichia coli

<400> SEQUENCE: 60

```
atggccaaag aagacaatat tgaaatgcaa ggaaccgttc ttgaaacgtt gcctaatacc      60
atgttccgcg tagagttaga aaacggtcac gtggttactg cacacatctc cggtaaaatg     120
cgcaaaaact acatccgcat cctgacgggc gacaaagtga ctgttgaact gaccccgtac     180
gacctgagca aaggccgcat tgtcttccgt agtcgctga                            219
```

<210> SEQ ID NO 61
<211> LENGTH: 567
<212> TYPE: DNA
<213> ORGANISM: Unknown
<220> FEATURE:
<223> OTHER INFORMATION: efp sequence originated from Escherichia coli

<400> SEQUENCE: 61

```
atggcaacgt actatagcaa cgatttcgt gctggtctta aaatcatgtt agacggcgaa       60
ccttacgcgg ttgaagcgag tgaattcgta aaaccgggta aaggccaggc atttgctcgc    120
gttaaactgc gtcgtctgct gaccggtact cgcgtagaaa aaccttcaa atctactgat      180
tccgctgaag cgctgatgt tgtcgatatg aacctgactt acctgtacaa cgacggtgag     240
ttctggcact tcatgaacaa cgaaactttc gagcagctgt ctgctgatgc aaaagcaatt    300
ggtgacaacg ctaaatggct gctggatcag gcagagtgta cgtaactct gtggaatgg      360
cagccgatct ccgttactcc gccgaacttc gttgaactgg aaatcgttga taccgatccg    420
ggcctgaaag gtgataccgc aggtactggt ggcaaaccgg ctaccctgtc tactggcgct    480
gtggttaaag ttccgctgtt tgtacaaatc ggcgaagtca tcaaagtgga tacccgctct   540
ggtgaatacg tctctcgcgt gaagtaa                                        567
```

<210> SEQ ID NO 62
<211> LENGTH: 720
<212> TYPE: DNA
<213> ORGANISM: Artificial Sequence
<220> FEATURE:
<223> OTHER INFORMATION: eGFP sequence

<400> SEQUENCE: 62

```
atggctagca agggcgagga gctgttcacc ggggtggtgc ccatcctggt cgagctggac      60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtga    720
```

<210> SEQ ID NO 63
<211> LENGTH: 711

<212> TYPE: DNA
<213> ORGANISM: Artificial Sequence
<220> FEATURE:
<223> OTHER INFORMATION: mCherry sequence

<400> SEQUENCE: 63

```
atggtttcca agggcgagga ggataacatg gctatcatta aagagttcat gcgcttcaaa      60
gttcacatgg agggttctgt taacggtcac gagttcgaga tcgaaggcga aggtgagggc     120
cgtccgtatg aaggcaccca gaccgccaaa ctgaaagtga ctaaaggcgg cccgctgcct     180
tttgcgtggg acatcctgag cccgcaattt atgtacggtt ctaaagctta tgttaaacac     240
ccagcggata tcccggacta tctgaagctg tcttttccgg aaggtttcaa gtgggaacgc     300
gtaatgaatt ttgaagatgg tggtgtcgtg accgtcactc aggactcctc cctgcaggat     360
ggcgagttca tctataaagt taaactgcgt ggtactaatt ttccatctga tggcccggtg     420
atgcagaaga gacgatgggt tgggaggcg tctagcgaac gcatgtaccc ggaagatggt     480
gcgctgaaag cgaaattaa acagcgcctg aaactgaaag atggcggcca ttatgacgct     540
gaagtgaaaa ccacgtacaa agccaagaaa cctgtgcagc tgcctggcgc gtacaatgtg     600
aatattaaac tggacatcac ctctcataat gaagattata cgatcgtaga gcaatatgag     660
cgcgcggagg gtcgtcattc taccggtggc atggatgagc tgtacaaata a              711
```

<210> SEQ ID NO 64
<211> LENGTH: 1473
<212> TYPE: DNA
<213> ORGANISM: Artificial Sequence
<220> FEATURE:
<223> OTHER INFORMATION: codon optimized cad sequence

<400> SEQUENCE: 64

```
atgaccaaac agagcgcaga tagcaatgca aaaagcggtg ttaccagcga aatttgtcat      60
tgggcaagca atctggcaac cgatgatatt ccgagtgatg ttctggaacg tgccaaatat     120
ctgattctgg atggtattgc atgtgcatgg ttggtgcac gtgttccgtg gtcagaaaaa     180
tatgttcagg caaccatgag ctttgaaccg cctggtgcat gtcgtgttat tggttatggc     240
cagaaactgg gtccggttgc agcagcaatg accaatagcg catttattca ggccaccgaa     300
ctggatgatt atcatagcga agcaccgctg catagcgcaa gcattgttct gcctgcagtt     360
tttgcagcaa gcgaagttct ggcagaacag ggtaaaacca ttagcggtat tgatgttatt     420
ctggcagcca ttgttggttt tgaaagcggt ccgcgtattg taaagcaat ttatggtagc     480
gatctgctga ataatggttg gcattgtggt cagtttatg gtgcaccggc aggcgcactg     540
gccaccggta aactgctggg tctgacaccg gatagcatgg aagatgcact gggtattgcc     600
tgtacccagg catgtggtct gatgagcgca cagtatggtg gtatggttaa acgtgttcag     660
catggttttg cagcccgtaa tggtctgctg gtggcctgc tggcacatgg tggttatgaa     720
gcaatgaaag gtgtgctgga acgtagctat ggtggttttc tgaaaatgtt taccaaaggc     780
aatggtcgtg aacctccgta taagaagaa gaagttgttg caggtctggg tagcttttgg     840
cataccttta ccattcgcat taaactgtat gcatgttgtg gtctggttca tggtccggtg     900
gaagcaattg aaaatctgca gggtcgttat ccggaactgc tgaatcgtgc aaatctgagc     960
aatattcgtc atgttcatgt tcagctgagc accgcaagca atagccattg cggttggatt    1020
ccggaagaac gtccgattag cagcattgca ggtcagatga cgttgcata tattctggcc    1080
gttcagctgg ttgatcagca gtgtctgctg agccagttta gcgaatttga tgataacctg    1140
```

| | |
|---|---|
| gaacgtccgg aagtttggga tctggcacgt aaagttacca gcagccagag cgaagaattt | 1200 |
| gatcaggatg gtaattgtct gagcgcaggt cgtgttcgta ttgaatttaa tgatggttcc | 1260 |
| agcattaccg aaagcgttga aaaccgctg ggtgttaaag aaccgatgcc gaatgaacgt | 1320 |
| atcctgcata aatatcgtac cctggcaggt agcgttaccg atgaaagccg tgtgaaagaa | 1380 |
| attgaagatc tggttctggg tctggatcgt ctgaccgata ttagtccgct gctggaactg | 1440 |
| ctgaactgtc cggttaaaag tccgctggtt taa | 1473 |

<210> SEQ ID NO 65
<211> LENGTH: 549
<212> TYPE: DNA
<213> ORGANISM: Unknown
<220> FEATURE:
<223> OTHER INFORMATION: idi sequence originated from Escherichia coli

<400> SEQUENCE: 65

| | |
|---|---|
| atgcagaccg aacatgtgat tctgctgaac gcgcagggcg tgccgaccgg caccctggaa | 60 |
| aaatatgcgg cgcataccgc ggatacccgc ctgcatctgg cgtttagcag ctggctgttt | 120 |
| aacgcgaaag ccagctgct ggtgacccgc cgcgcgctga gcaaaaaagc gtggccgggc | 180 |
| gtgtggacca acagcgtgtg cggccatccg cagctgggcg aaagcaacga agatgcggtg | 240 |
| attcgccgct ccgctatga actgggcgtg gaaattaccc cgccggaaag catttatccg | 300 |
| gattttcgct atcgcgcgac cgatccgagc ggcattgtgg aaaacgaagt gtgcccggtg | 360 |
| tttgcggcgc gcaccaccag cgcgctgcag attaacgatg atgaagtgat ggattatcag | 420 |
| tggtgcgatc tggcggatgt gctgcatggc attgatgcga ccccgtgggc gtttagcccg | 480 |
| tggatggtga tgcaggcgac caaccgcgaa gcgcgcaaac gcctgagcgc gtttacccag | 540 |
| ctgaaataa | 549 |

<210> SEQ ID NO 66
<211> LENGTH: 900
<212> TYPE: DNA
<213> ORGANISM: Unknown
<220> FEATURE:
<223> OTHER INFORMATION: ispA sequence originated from Escherichia coli

<400> SEQUENCE: 66

| | |
|---|---|
| atggatttcc cgcagcagct ggaagcgtgt gtgaaacagg cgaaccaggc gctgagccgc | 60 |
| tttattgcgc cgctgccgtt tcagaacacc ccggtggtgg aaaccatgca gtatggcgcg | 120 |
| ctgctgggcg gcaaacgcct gcgcccgttt ctggtgtatg cgaccggcca catgtttggc | 180 |
| gtgagcacca cacccctgga tgcgccggcg gcggcggtgg aatgcattca tgcgtatagc | 240 |
| ctgattcatg atgatctgcc ggcgatggat gatgatgatc tgcgccgcgg cctgccgacc | 300 |
| tgccatgtga atttggcga agcgaacgcg attctggcgg gcgatgcgct gcagaccctg | 360 |
| gcgtttagca ttctgagcga tgcggatatg ccggaagtga gcgatcgcga tcgcattagc | 420 |
| atgattagcg aactggcgag cgcgagcggc attgcgggca tgtgcggcgg ccaggcgctg | 480 |
| gatctggatg cggaaggcaa acatgtgccg ctggatgcgc tggaacgcat tcatcgccat | 540 |
| aaaaccggcg cgctgattcg cgcggcgtg gccctgggcg cgctgagcgc gggcgataaa | 600 |
| ggccgccgcg cgctgccggt gctggataaa tatgcggaaa gcattggcct ggcgtttcag | 660 |
| gtgcaggatg atattctgga tgtggtgggc gataccgcga ccctgggcaa acgccagggc | 720 |
| gcggatcagc agctgggcaa aagcacctat ccggcgctgc tgggcctgga acaggcgcgc | 780 |
| aaaaagcgc gcgatctgat tgatgatgcg cgccagagcc tgaaacagct ggcggaacag | 840 |

```
agcctggata ccagcgcgct ggaagcgctg gcggattata ttattcagcg caacaaataa      900
```

<210> SEQ ID NO 67
<211> LENGTH: 924
<212> TYPE: DNA
<213> ORGANISM: Artificial Sequence
<220> FEATURE:
<223> OTHER INFORMATION: crtE sequence originated from Pantoea
      agglomerans

<400> SEQUENCE: 67

```
atggtatctg gctcaaaggc tggcgtctcg ccacatcgcg aaattgaagt gatgcgccag       60
agcattgatg atcatctggc gggcctgctg ccggaaaccg atagccagga tattgtgagc      120
ctggcgatgc gcgaaggcgt gatggcgccg ggcaaacgca ttcgcccgct gctgatgctg      180
ctggcggcgc gcgatctgcg ctatcagggc agtatgccga ccctgctgga tctggcgtgc      240
gcggtggaac tgacccatac cgcgagcctg atgctggatg atatgccgtg catggataac      300
gcggaactgc gccgcggcca gccgaccacc cataaaaaat tggcgaaaag cgtggcgatt      360
ctggcgagcg tgggcctgct gagcaaagcg tttggcctga ttgcggcgac cggcgatctg      420
ccgggcgaac gccgcgcgca ggcggtgaac gaactgagca ccgcggtggg cgtgcagggc      480
ctggtgctgg ccagtttccg cgatctgaac gatgcggcgc tggatcgcac cccggatgcg      540
attctgagca ccaaccatct gaaaaccggc attctgttta gcgcgatgct gcagattgtg      600
gcgattgcga gcgcgagcag cccgagcacc cgcgaaaccc tgcacgcgtt tgcgctggat      660
tttggccagg cgtttcagct gctggatgat ctgcgcgatg atcatccgga aaccggcaaa      720
gatcgcaaca agatgcgggg caaaagcacc ctggtgaacc gcctgggcgc ggatgcggcg      780
cgccagaaac tgcgcgaaca tattgatagc gcggataaac atctgacctt tgcgtgcccg      840
cagggcggcg cgattcgcca gtttatgcat ctgtggtttg gccatcatct ggcggattgg      900
agcccggtga tgaaaattgc gtaa                                             924
```

<210> SEQ ID NO 68
<211> LENGTH: 930
<212> TYPE: DNA
<213> ORGANISM: Artificial Sequence
<220> FEATURE:
<223> OTHER INFORMATION: crtB sequence originated from Pantoea
      agglomerans

<400> SEQUENCE: 68

```
atgtcccaac ccccttgct agaccacgca acccagacga tggcgaacgg cagcaagagc        60
tttgcgaccg cggcgaaact gtttgatccg gcgacccgcc gcagcgtgct gatgctgtat      120
acctggtgcc gccattgcga tgatgtgatt gatgatcaga cgcatggctt tgcgagcgaa      180
gcggcggcgg aagaagaagc gacccagcgc ctggcgcgcc tgcgcaccct gacctggcg       240 gcgtttgaag cgcggaaat gcaggacccg cgtttgcgg cgtttcagga agtggcgctg        300
acccacggca ttacccgcg catggcgctg gatcatctgg atggctttgc gatggatgtg       360
gcgcagaccc gctatgtgac ctttgaagat accctgcgct attgctatca tgtggcgggc      420
gtggtgggcc tgatgatggc gcgcgtgatg ggcgtgcgcg atgaacgcgt gctggatcgc      480
gcgtgcgatc tgggcctggc gtttcagctg accaacattg cgcgcgatat tattgatgat      540
gcggcgattg atcgctgcta tctgccgcg gaatggctgc aggatgcggg cctgaccccg      600
gaaaactatg cggcgcgcga aaaccgcgcg ggcctggcgc gcgtggcgga acgcctgatt      660
```

```
gatgcggcgg aaccgtatta tattagcagc caggcgggcc tgcatgatct gccgccgcgc    720
tgcgcgtggg cgattgcgac cgcgcgcagc gtgtatcgcg aaattggcat taaagtgaaa    780
gcggcgggcg gcagcgcgtg ggatcgccgc cagcatacca gcaaaggcga aaaaattgcg    840
atgctgatgg cggcgccggg ccaggtgatt cgcgcgaaaa ccacccgcgt gaccccgcgc    900
ccggcgggcc tgtggcagcg cccggtgtaa                                     930
```